US011766245B2

(12) United States Patent
Abe

(10) Patent No.: US 11,766,245 B2
(45) Date of Patent: Sep. 26, 2023

(54) ULTRASONIC DIAGNOSTIC APPARATUS AND CONTROL METHOD

(71) Applicant: Toshiba Medical Systems Corporation, Otawara (JP)

(72) Inventor: Yasuhiko Abe, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1209 days.

(21) Appl. No.: 15/069,489

(22) Filed: Mar. 14, 2016

(65) Prior Publication Data

US 2016/0331349 A1 Nov. 17, 2016

(30) Foreign Application Priority Data

May 15, 2015 (JP) ................................ 2015-100402

(51) Int. Cl.
*A61B 8/08* (2006.01)
*A61B 8/00* (2006.01)
*A61B 5/318* (2021.01)

(52) U.S. Cl.
CPC ............ *A61B 8/5223* (2013.01); *A61B 5/318* (2021.01); *A61B 8/0883* (2013.01); *A61B 8/463* (2013.01); *A61B 8/4444* (2013.01); *A61B 8/5207* (2013.01); *A61B 8/54* (2013.01)

(58) Field of Classification Search
CPC .................................................. A61B 8/0883
See application file for complete search history.

(56) References Cited

U.S. PATENT DOCUMENTS 7,711,160 B2 * 5/2010 O'Donnell ................ G06T 7/12 382/128
8,496,590 B2 7/2013 Abe
2011/0082371 A1 * 4/2011 Chono .................. G06T 7/0012 600/443

(Continued)

FOREIGN PATENT DOCUMENTS

CN 102958448 * 3/2013 ........... A61B 8/5223
JP 2011-72656 A 4/2011
JP 2013-226400 A 11/2013

(Continued)

OTHER PUBLICATIONS

Japanese Office Action dated Dec. 11, 2018 in Japanese Patent Application No. 2015-100402, 3 pages.

(Continued)

*Primary Examiner* — Rochelle D Turchen
(74) *Attorney, Agent, or Firm* — Oblon, McClelland, Maier & Neustadt, L.L.P.

(57) ABSTRACT

An ultrasonic diagnostic apparatus according to an embodiment comprises an ultrasonic probe, image generation circuitry, and processing circuitry. The ultrasonic probe performs ultrasonic scanning on a two-dimensional region of a subject. The image generation circuitry generates ultrasonic image data corresponding to the two-dimensional region. The processing circuitry calculates a characteristic amount of a structure that is detected from each of a plurality of pieces of ultrasonic image data generated by the ultrasonic scanning at different positions. The processing circuitry outputs information based on a comparison result of the calculated characteristic amounts.

6 Claims, 11 Drawing Sheets

(56) References Cited

U.S. PATENT DOCUMENTS

2015/0038846 A1 2/2015 Abe et al.

FOREIGN PATENT DOCUMENTS

WO WO-2013146710 A1 * 10/2013 ........... A61B 8/0883
WO WO-2014059170 A1 * 4/2014 ........... A61B 5/1102

OTHER PUBLICATIONS

Shuhei Nitta, et al. "Automatic slice alignment method for cardiac magnetic resonance imaging", Magnetic Resonance Materials in Physics, Biology and Medicine, Total 13 Pages, (Jan. 26, 2013).
Takamasa Sugiura, et al., "Automatic model-based contour detection of left ventricle myocardium from cardiac CT images", International Journal of Computer Assisted Radiology and Surgery, Total 13 Pages, (May 1, 2012).

* cited by examiner 1
100
APPARATUS MAIN BODY
13
DISPLAY
12
INPUT DEVICE
170
PROCESSING CIRCUITRY
171
CALCULATION FUNCTION
172
OUTPUT CONTROL FUNCTION
173
STORAGE FUNCTION
120
B-MODE PROCESSING CIRCUITRY
130
DOPPLER PROCESSING CIRCUITRY
110
TRANSMISSION/ RECEPTION CIRCUITRY
140
IMAGE GENERATION CIRCUITRY
150
IMAGE MEMORY
160
STORAGE CIRCUITRY
14
ELECTRO-CARDIOGRAPH
11
ULTRASONIC PROBE
P

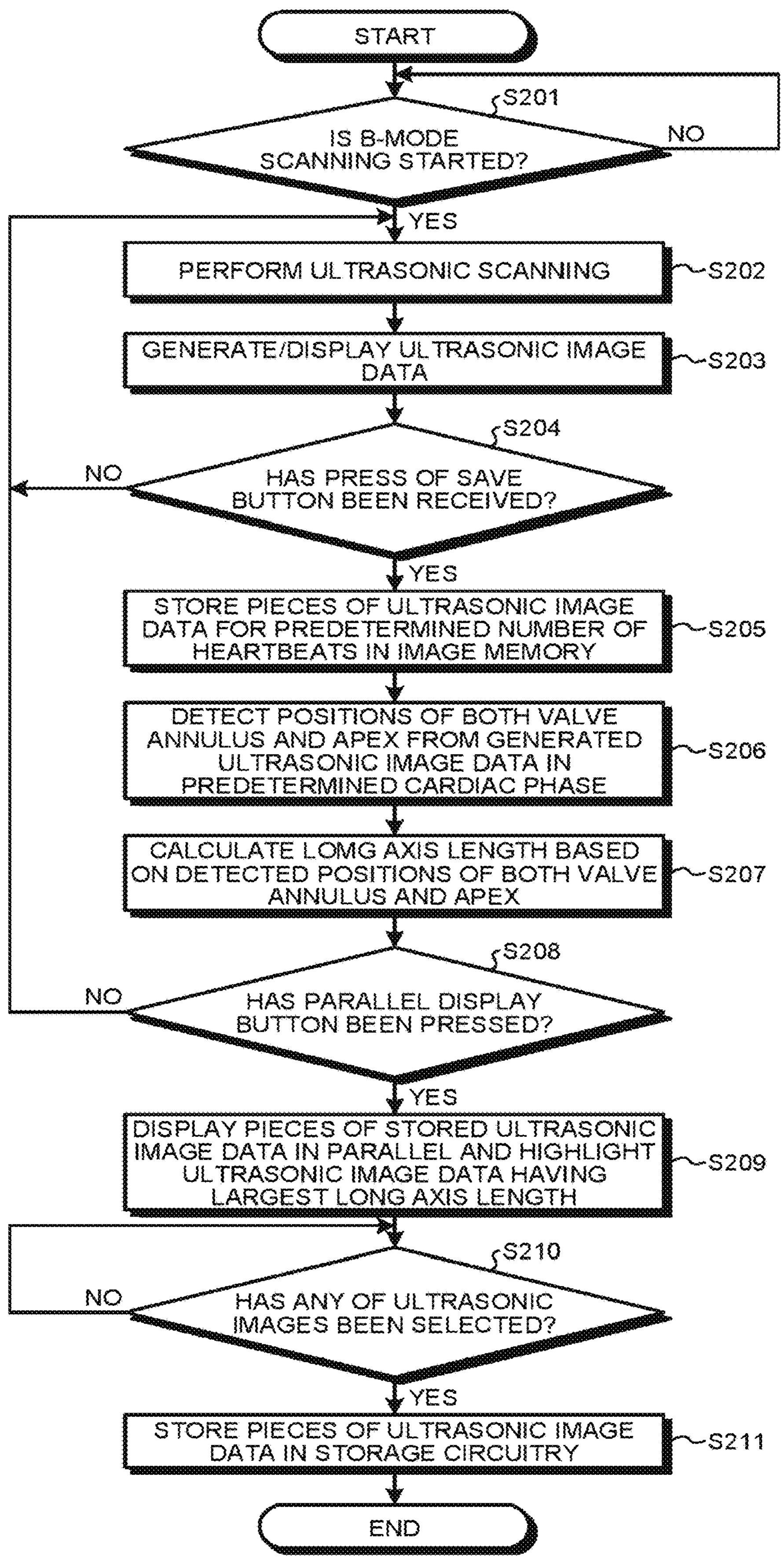
FIG.7
START
S201
IS B-MODE SCANNING STARTED?
NO
YES
PERFORM ULTRASONIC SCANNING
S202
GENERATE/DISPLAY ULTRASONIC IMAGE DATA
S203
S204
HAS PRESS OF SAVE BUTTON BEEN RECEIVED?
NO
YES
STORE PIECES OF ULTRASONIC IMAGE DATA FOR PREDETERMINED NUMBER OF HEARTBEATS IN IMAGE MEMORY
S205
DETECT POSITIONS OF BOTH VALVE ANNULUS AND APEX FROM GENERATED ULTRASONIC IMAGE DATA IN PREDETERMINED CARDIAC PHASE
S206
CALCULATE LOMG AXIS LENGTH BASED ON DETECTED POSITIONS OF BOTH VALVE ANNULUS AND APEX
S207
S208
HAS PARALLEL DISPLAY BUTTON BEEN PRESSED?
NO
YES
DISPLAY PIECES OF STORED ULTRASONIC IMAGE DATA IN PARALLEL AND HIGHLIGHT ULTRASONIC IMAGE DATA HAVING LARGEST LONG AXIS LENGTH
S209
S210
HAS ANY OF ULTRASONIC IMAGES BEEN SELECTED?
NO
YES
STORE PIECES OF ULTRASONIC IMAGE DATA IN STORAGE CIRCUITRY
S211
END 13
55
current
Center
Length
A4C
diff
=XX
54
50
52
Center
Length
A2C
51
53

1
100
APPARATUS MAIN BODY
P
14
ELECTRO-CARDIOGRAPH
11
ULTRASONIC PROBE
110
TRANSMISSION/RECEPTION CIRCUITRY
120
B-MODE PROCESSING CIRCUITRY
130
DOPPLER PROCESSING CIRCUITRY
140
IMAGE GENERATION CIRCUITRY
150
IMAGE MEMORY
160
STORAGE CIRCUITRY
13
DISPLAY
12
INPUT DEVICE
170
PROCESSING CIRCUITRY
CALCULATION FUNCTION
171
OUTPUT CONTROL FUNCTION
172
STORAGE FUNCTION
173
SCAN CONTROL FUNCTION
174

ULTRASONIC DIAGNOSTIC APPARATUS AND CONTROL METHOD

CROSS-REFERENCE TO RELATED APPLICATIONS

This application is based upon and claims the benefit of priority from Japanese Patent Application No. 2015-100402, filed on May 15, 2015; the entire contents of which are incorporated herein by reference.

FIELD

Embodiments described herein relate generally to an ultrasonic diagnostic apparatus and a control method.

BACKGROUND

Conventionally, in echocardiography with an ultrasonic diagnostic apparatus, cardiac function evaluation of various types using apical long axis images (apical four-chamber view (A4C) image, apical two-chamber view (A2C) image, and the like) that are provided by two-dimensional ultrasonic scanning has been performed. The cardiac function evaluation is performed by a method using, as indicators, volume information (end diastolic volume (EDV), end systolic volume (ESV), or ejection fraction (EF)) of a left ventricle by a modified Simpson method and global longitudinal strain (GLS) information provided by a Speckle Tracking method, for example. To be specific, effect determination, cardiotoxicity evaluation, and the like of medication are performed using the EF and the GLS. For example, for cases for which the cardiac function evaluation is performed, variation of the cardiac function is diagnosed by following up the above-mentioned indicators for a long period of time. Diagnosis by accurately detecting a small variation of the cardiac function is required depending on cases.

BRIEF DESCRIPTION OF THE DRAWINGS

FIG. 7 is an exemplary flowchart illustrating processing procedures by an ultrasonic diagnostic apparatus in the second embodiment;

DETAILED DESCRIPTION

An ultrasonic diagnostic apparatus according to an embodiment comprises an ultrasonic probe, image generation circuitry, and processing circuitry. The ultrasonic probe performs ultrasonic scanning on a two-dimensional region of a subject. The image generation circuitry generates ultrasonic image data corresponding to the two-dimensional region. The processing circuitry calculates a characteristic amount of a structure that is detected from each of a plurality of pieces of ultrasonic image data generated by the ultrasonic scanning at different positions. The processing circuitry outputs information based on a comparison result of the calculated characteristic amounts.

The following describes the ultrasonic diagnostic apparatus and a control program according to embodiments with reference to the accompanying drawings.

First Embodiment

Figure 1:
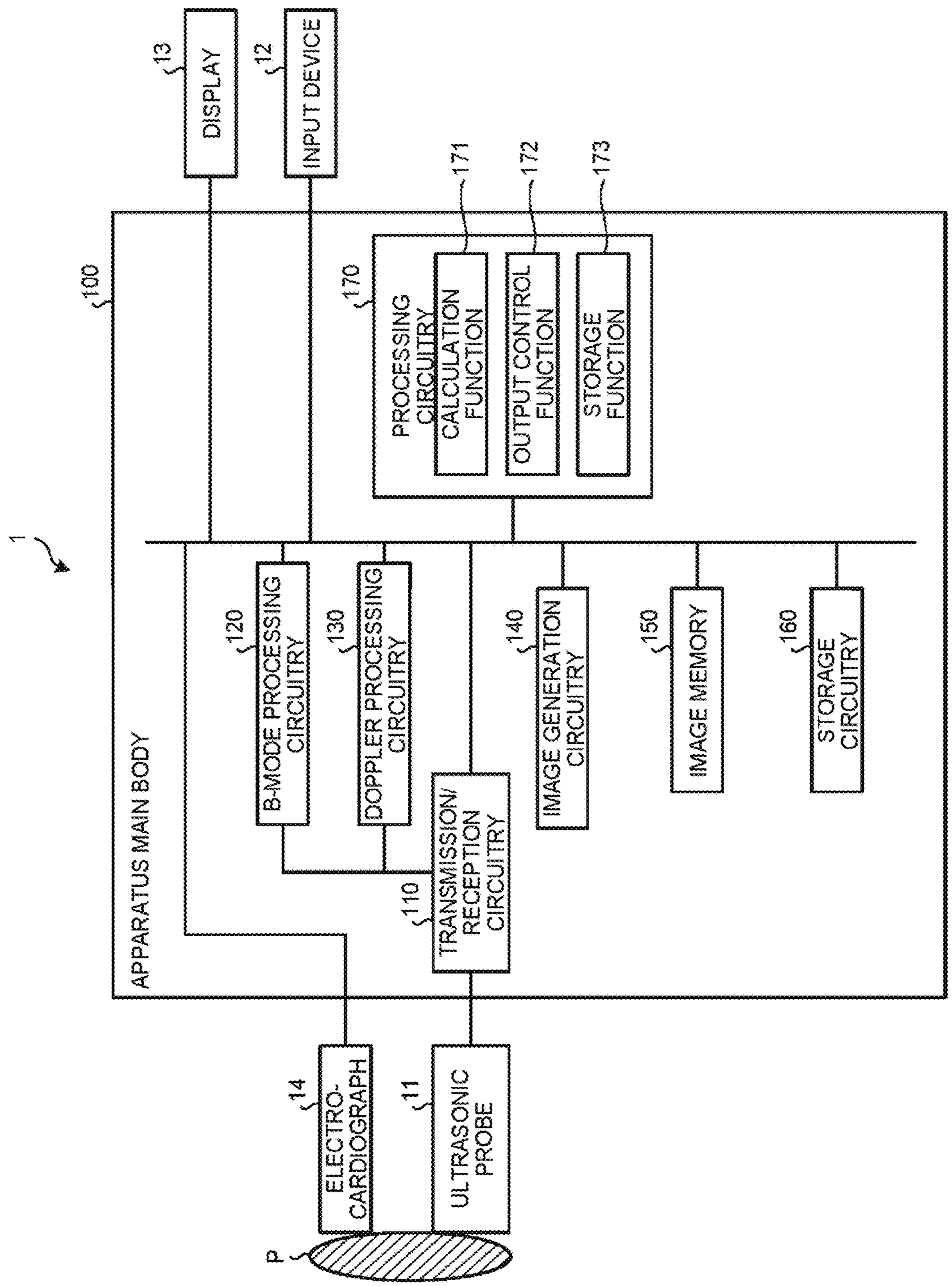
FIG. 1 is an exemplary block diagram illustrating an example of the configuration of an ultrasonic diagnostic apparatus according to a first embodiment.

FIG. 1 is a block diagram illustrating an example of the configuration of an ultrasonic diagnostic apparatus 1 according to a first embodiment. As illustrated in FIG. 1, the ultrasonic diagnostic apparatus 1 in the first embodiment comprises an ultrasonic probe 11, an input device 12, a display 13, an electrocardiograph 14, and an apparatus main body 100. The ultrasonic probe 11 is connected to transmission/reception circuitry 110 in the apparatus main body 100, which will be described later, in a communicable manner. The input device 12, the display 13, and the electrocardiograph 14 are connected to circuitry of various types that are in the apparatus main body 100 in a communicable manner.

The ultrasonic probe 11 is brought into contact with a body surface of a subject P and transmits and receives ultrasonic waves. For example, the ultrasonic probe 11 comprises a plurality of piezoelectric transducer elements. These piezoelectric transducer elements generate the ultrasonic waves based on a driving signal that is supplied from the transmission/reception circuitry 110. The generated ultrasonic waves are reflected by tissues in the body of the subject P and are received by the piezoelectric transducer elements as reflected wave signals. The ultrasonic probe 11 transmits the reflected wave signals received by the piezoelectric transducer elements to the transmission/reception circuitry 110.

The ultrasonic probe 11 in the first embodiment performs ultrasonic scanning on a two-dimensional region. For example, the ultrasonic probe 11 is a one-dimensional (1D) array probe in which the piezoelectric transducer elements are arranged one-dimensionally. The ultrasonic probe 11 performs the ultrasonic scanning in a state of being brought into contact with the body surface at a position (near the chest) capable of providing an apical approach image (apical four-chamber view (A4C) image, apical two-chamber view (A2C) image, or the like) by scanning. An operator appropriately changes a position and an angle of the ultrasonic probe 11.

The input device 12 corresponds to a mouse, a keyboard, a button, a panel switch, a touch command screen, a foot switch, a track ball, or a joystick, for example. The input device 12 receives setting requests of various types from the operator of the ultrasonic diagnostic apparatus 1 and appropriately transfers the received setting requests of various types to the circuitry of the apparatus main body 100.

The display 13 displays a graphical user inter ace (GUI) for enabling the operator to input the setting requests of various types using the input device 12, an image (ultrasonic image) based on the ultrasonic image data generated by the apparatus main body 100, and the like.

The electrocardiograph 14 acquires an electrocardiogram (ECG) of the subject as an electrocardiogram signal of the subject P for which the ultrasonic scanning is performed. The electrocardiograph 14 appropriately transmits the acquired electrocardiogram to the circuitry of the apparatus main body 100.

The apparatus main body 100 is a device that generates the ultrasonic image data based on the reflected wave signals received by the ultrasonic probe 11. As illustrated FIG. 1, the apparatus main body 100 comprises the transmission/reception circuitry 110, B-mode processing circuitry 120, Doppler processing circuitry 130, an image generation circuitry 140, an image memory 150, storage circuitry 160, and processing circuit 170. The transmission/reception circuitry 110, the B-mode processing circuitry 120, the Doppler processing circuitry 130, the image generation circuitry 140, the image memory 150, the storage circuitry 160, and the processing circuitry 170 are connected to one another in a communicable manner.

The transmission/reception circuitry 110 controls transmission and reception of the ultrasonic waves by the ultrasonic probe 11. For example, the transmission/reception circuitry 110 controls the transmission and reception of the ultrasonic waves that are performed by the ultrasonic probe 11 based on instructions from the processing circuitry 170, which will be described later. The transmission/reception circuitry 110 applies the driving signal (driving pulse) to the ultrasonic probe 11 so as to cause the ultrasonic probe 11 to transmit ultrasonic beams formed by collecting the ultrasonic waves in a beam form. The transmission/reception circuitry 110 performs addition processing by applying predetermined delay times to the reflected wave signals received by the ultrasonic probe 11 so as to generate reflected wave data with an enhanced reflection component from a direction in accordance with reception directivity of the reflected wave signals and transmits the generated reflected wave data to the B-mode processing circuitry 120 and the Doppler processing circuitry 130.

The B-mode processing circuitry 120 performs pieces of signal processing of various types on the reflected wave data that the transmission/reception circuitry 110 has generated from the reflected wave signals. The B-mode processing circuitry 120 performs logarithmic amplification, envelope detection processing, and the like on the reflected wave data received from the transmission/reception circuitry 110 so as to generate data (B-mode data) representing a signal intensity for each sampling point (observation point) by a luminance. The B-mode processing circuitry 120 transmits the generated B-mode data to the image generation circuitry 140.

The Doppler processing circuitry 130 generates data (Doppler data) provided by extracting motion information based on the Doppler effect of a moving object at each sampling point in a scanning region from the reflected wave data received from the transmission/reception circuitry 110. To be specific, the Doppler processing circuitry 130 generates the Doppler data provided by extracting an average velocity, a variance, a power value, or the like, as the motion information of the moving object, at each sampling point. The moving object is blood flow, tissue such as a heart wall, and a contrast agent, for example. The Doppler processing circuitry 130 transmits the generated Doppler data to the image generation circuitry 140.

The image generation circuitry 140 generates the ultrasonic image data from the pieces of data generated by the B-mode processing circuitry 120 and the Doppler processing circuitry 130. For example, the image generation circuitry 140 generates B-mode image data representing the intensity of the reflected waves by the luminance from the B-mode data generated by the B-mode processing circuitry 120. The image generation circuitry 140 generates Doppler image data indicating moving object information from the Doppler data generated by the Doppler processing circuitry 130. The Doppler image data is velocity image data, variance image data, power image data, or image data formed by combining them. It should be noted that the image generation circuitry 140 is an example of an image generator.

The image memory 150 is a memory storing therein pieces of data generated by the B-mode processing circuitry 120, the Doppler processing circuitry 130, and the image generation circuitry 140. For example, the image memory 150 stores therein the ultrasonic image data generated by the image generation circuitry 140 so as to correspond to the electrocardiogram of the subject P. When a data amount that is stored in the image memory 150 exceeds a storage capacity of the image memory 150, data is deleted in the order from oldest data and is updated.

The storage circuitry 160 is a storage device storing therein pieces of data of various types. For example, the storage circuitry 160 stores therein control programs for performing the transmission and reception of the ultrasonic waves, the image processing, and display processing, pieces of data of various types such as diagnostic information (for example, patient ID and doctor's observation), diagnostic protocols, and body marks of various types. The pieces of data that are stored in the storage circuitry 160 can be transferred to an external device through an interface unit (not illustrated).

The storage circuitry 160 stores therein pieces of data generated by the B-mode processing circuitry 120, the Doppler processing circuitry 130, and the image generation circuitry 140. For example, the storage circuitry 160 stores therein the pieces of ultrasonic image data for the predetermined number of heartbeats specified by the operator.

The processing circuitry 170 controls the entire processing of the ultrasonic diagnostic apparatus 1. To be specific, the processing circuitry 170 controls pieces of processing of the transmission/reception circuitry 110, the B-mode processing circuitry 120, the Doppler processing circuitry 130, the image generation circuitry 140, and the like based on the setting requests of various types that have been input by the operator through the input device 12, and the control programs of various types and the pieces of data of various types that have been read from the storage circuitry 160. The processing circuitry 170 controls to display the ultrasonic image data that is stored in the image memory 150 on the display 13.

The processing circuitry 170 in the first embodiment comprises a calculation function 171, an output control function 172, and a storage function 173. Processing functions that are executed by the calculation function 171, the output control function 172, and the storage function 173 as components of the processing circuitry 170 are recorded in the storage circuitry 160 in forms of computer-executable programs, for example. The processing circuitry 170 is a processor that reads the computer programs from the storage circuitry 160 and executes them so as to cause the functions corresponding to the computer programs to operate. In other words, the processing circuitry 170 that has read the computer programs has the corresponding functions as illustrated in the processing circuitry 170 of FIG. 1. The individual functions of the calculation function 171, the output control function 172, and the storage function 173 will be described later.

Although the processing functions that are executed by the calculation function 171, the output control function 172, and the storage function 173 are implemented in the single processing circuitry 170 in FIG. 1, a plurality of independent processors may be combined to configure processing circuitry and these processors may execute the computer programs so as to cause the corresponding functions to operate.

The word "processor" used in the above description indicates a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processors read the computer programs stored in the storage circuitry and execute them so as to cause the corresponding functions to operate. Instead of storage of the computer programs in the storage circuitry 160, the computer programs may be directly incorporated in circuitry of the processors. In this case, the processors read and execute the computer programs incorporated in the circuitry so as to cause the corresponding functions to operate. The processors in the embodiment are not limited to be configured as single circuitry for the respective processors. A plurality of independent circuitry may be combined to configure one processor and the processor may cause functions thereof to operate. The components in FIG. 1 may be integrated into one processor and the processor may cause the functions thereof to operate.

In the conventional cardiac function evaluation, it has been, however, difficult to provide a desired cross section accurately in some cases. For example, when the apical approach image (apical four-chamber view (A4C) image, apical two-chamber view (A2C) image, or the like) is captured by two-dimensional ultrasonic scanning, an ultrasonic image passing through the vicinity of an apex is provided while a scanned cross section does not pass through the apex in some cases. In this case, in the provided ultrasonic image, a contour of the vicinity of the apex is seen almost like a contour provided by drawing the apex rightly and the operator cannot therefore determine whether the ultrasonic image passes through the apex accurately. When a desired cross section cannot be provided accurately as described above, accurate values cannot be provided even when the indicators such as the ejection fraction (EF) and the global longitudinal strain (GLS) are calculated. As a result, even when the cardiac function changes, for example, the change is possibly unnoticed.

Moreover, for example, the same operator does not always perform tests (image capturing) in follow-up for a long period of time. For this reason, it has been difficult to provide a cross section identical to that provided by the past image capturing in some cases. For example, when an operator who performs the test at this time is different from an operator that has performed the test at the previous time, it is difficult to provide a cross section identical to that provided by the previous image capturing accurately because recognition of the apex that is drawn onto the ultrasonic image is different between the operators. When the cross section identical to that provided by the previous image capturing cannot be provided accurately, variation in measured values occurs even when the indicators such as the EF and the GLS are calculated. For this reason, even when the cardiac function changes, for example, the change is possibly unnoticed.

Usage of volume data as three-dimensional ultrasonic image data is considered to be a measure against the above-mentioned problem. The volume data cannot, however, provide spatial resolution and temporal resolution as high as those that are provided by the two-dimensional ultrasonic scanning in some cases. Insufficient spatial resolution causes a position of an endocardium of the heart to blur. For example, a position of a lumen is recognized at the inner side relative to an actual position, resulting in undervaluation of a volume thereof in some cases. Insufficient temporal resolution causes a cardiac phase in which the cardiac function is evaluated to vary in some cases. As described above, even usage of the volume data cannot necessarily provide stable values. Furthermore, the usage of the volume data requires an expensive apparatus configuration comprising a 2D array probe in which piezoelectric transducer elements are arranged two-dimensionally in a lattice form, and other components.

In consideration of these inconvenience, the ultrasonic diagnostic apparatus 1 in the first embodiment executes the functions as will be described later in order to provide a desired cross section accurately. That is to say, the ultrasonic diagnostic apparatus 1 in the first embodiment displays, on a two-dimensional ultrasonic image displayed substantially real time, an increase/decrease extent of a long axis of a left ventricle that is displayed on the current ultrasonic image relative to the long axis displayed previously. The long axis length of the left ventricle is the largest on a cross section passing through the apex. Based on this, the operator can provide the cross section with the longest long axis, that is, the cross section passing through the apex accurately by gradually changing the position and the angle of the ultrasonic probe 11 while browsing the display.

The following embodiment describes the case where the ultrasonic diagnostic apparatus 1 displays information related to the long axis of the left ventricle when the operator performs the ultrasonic scanning on a plurality of cross sections in the vicinity of a cross section as a reference, as an example. In other words, the operator moves the ultrasonic probe 11 to a position at which the desired cross section can be considered to be provided and browses the information related to the long axis based on the cross section obtained at the position. The operator further changes the position and the angle of the ultrasonic probe 11 while browsing the display so as to provide the cross section passing through the apex as the desired cross section.

Although a cross section (A4C image) passing through the apex of the heart of the subject P is provided accurately in the following embodiments, embodiments are not limited thereto. For example, the first embodiment is not limited to be applied to the heart and may be applied to other structures, and is not limited to be applied to the long axis of the left ventricle and may be applied to other characteristic amounts.

The calculation function 171 is a function that is implemented when the processing circuitry 170 reads a computer program corresponding to the calculation function 171 from the storage circuitry 160 and executes it. The calculation function 171 calculates a characteristic amount of a structure that is detected from each of a plurality of pieces of ultrasonic image data generated by the ultrasonic scanning at different timings. For example, the calculation function 171 specifies ultrasonic image data in a predetermined cardiac phase based on an electrocardiogram signal that is detected from the subject P and calculates the characteristic amount from the specified ultrasonic image data. To be specific, the calculation function 171 acquires the electrocardiogram of the subject P from the electrocardiograph 14 and calculates time at which an R wave is detected using the acquired electrocardiogram. Then, the calculation function 171 specifies the ultrasonic image data generated by the image generation circuitry 140 at the calculated time as the ultrasonic image data in the R-wave time phase. The calculation function 171 is an example of a calculator.

Subsequently, the calculation function 171 detects positions of a valve ring (valve annulus) and the apex of the heart from the pieces of ultrasonic image data and calculates the length of the long axis (long axis length) of the left ventricle based on the detected positions of the valve ring and the apex. As an example, the calculation function 171 detects the positions of the valve annulus and the apex contained in the two-dimensional ultrasonic image data using knowledge based learning algorithm with a teacher. The knowledge based learning algorithm with the teacher uses a recognition-type database constructed using a plurality of teacher images (ultrasonic images) in which accurate positions of the valve annulus and the apex are set. Then, the calculation function 171 calculates the long axis length of the left ventricle based on the detected positions of the valve annulus and the apex.

Figure 2:
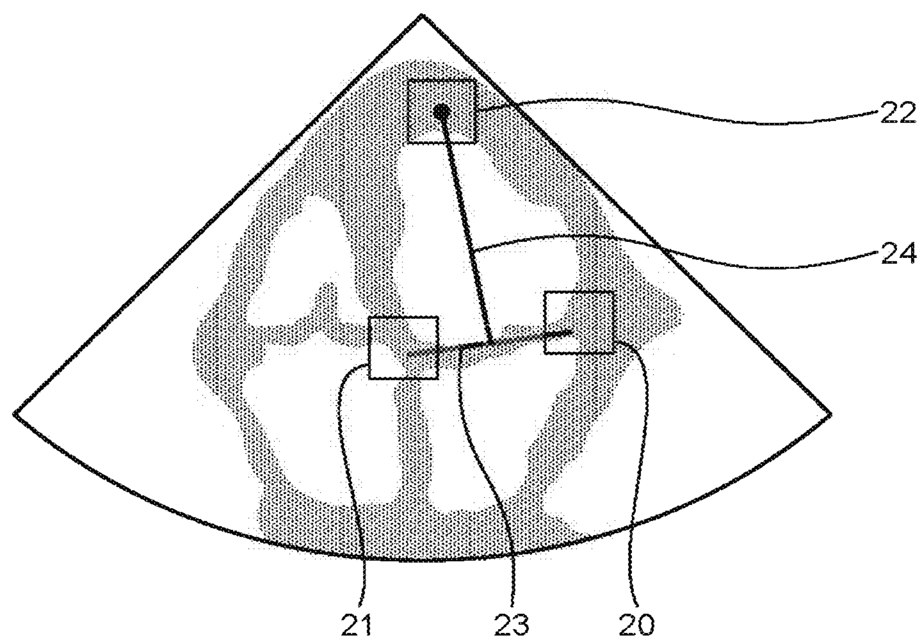
FIG. 2 is an exemplary view for explaining processing of a calculation function in the first embodiment.

FIG. 2 is a view for explaining processing of the calculation function 171 in the first embodiment. FIG. 2 schematically illustrates the processing of calculating the long axis length by the calculation function 171 on the A4C image.

As illustrated in FIG. 2, the calculation function 171 detects a position 20 of a mitral annulus at the lateral wall side, position 21 of a mitral annulus at the septum side, and a position 22 of the apex from the ultrasonic image data in the R-wave time phase that has been provided at a certain timing using the knowledge based learning algorithm with the teacher. The calculation function 171 calculates, as the long axis length, a length of a line segment 24 connecting the position 22 and a middle point of a line segment 23 connecting the detected position 20 and the detected position 21. The calculation function 171 calculates the long axis length in the same manner for pieces of ultrasonic image data in R-wave time phases that have been provided at other timings. When right and left mitral annulus are referred collectively in the following description, they are referred to as "valve annulus" or "both valve annulus".

Thus, the calculation function 171 calculates the long axis lengths for the pieces of ultrasonic image data in the R-wave time phases that have been provided at different timings. FIG. 2 is merely an example and, for example, the calculation function 171 may calculate the long axis lengths from the pieces of ultrasonic image data in cardiac phases other than the R-wave time phase.

The output control function 172 is a function that is implemented when the processing circuitry 170 reads the computer program corresponding to the output control function 172 from the storage circuitry 160 and executes it. The output control function 172 outputs information based on a comparison result of the characteristic amounts calculated by the calculation function 171. For example, the output control function 172 outputs information based on a comparison result of the characteristic amounts in the predetermined cardiac phases. The output control function 172 outputs increase/decrease information indicating an increase/decrease extent of the characteristic amount as the information based on the comparison result. The output control function 172 is an example of an output controller.

For example, the output control function 172 displays, as the increase/decrease information, long axis length information as information indicating an increase/decrease extent of the long axis length on a display screen of the display 13. Display examples of the long axis length information include "+++", "++", "+", "0", "−", "−−", and "−−−". Among them, "+++", "++", and "+" indicate that the long axis length calculated at the current timing is larger than the long axis length calculated at the previous timing and as the number of "+" is larger, a difference from the long axis length calculated at the previous timing is larger (that is, the long axis length calculated at the current timing is longer). "−−−", "−−", and "−" indicate that the long axis length calculated at the current timing is smaller than the long axis length calculated at the previous timing and as the number of "−" is larger, a difference from the long axis length calculated at the previous timing is larger (that is, the long axis length calculated at the current timing is smaller). "0" indicates that the long axis length calculated at the current timing is equivalent to the long axis length calculated at the previous timing.

Figure 3:
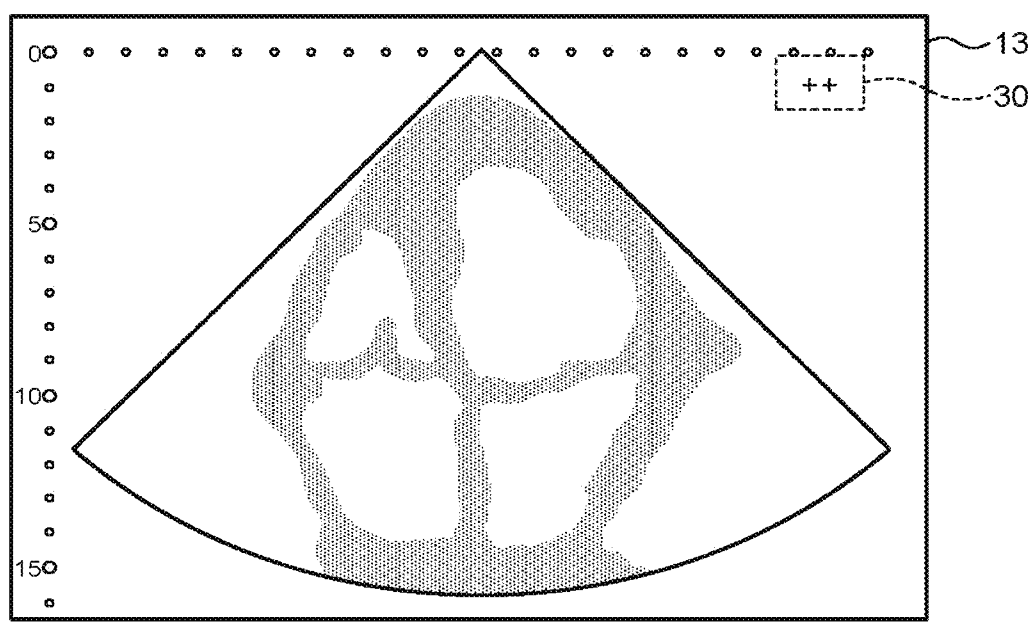
FIG. 3 is an exemplary view for explaining processing of an output control function in the first embodiment.

FIG. 3 is a view for explaining processing of the output control function 172 in the first embodiment. FIG. 3 illustrates the case where an image 30 indicating the long axis length information is displayed together with the A4C image that is displayed on the display screen of the display 13.

As illustrated in FIG. 3, when the image generation circuitry 140 generates the ultrasonic image data in the R-wave time phase, the output control function 172 acquires the long axis length corresponding to the ultrasonic image data from the calculation function 171. Then, the output control function 172 compares the acquired long axis length (that is, the current long axis length) and the long axis length calculated in the previous R-wave time phase. For example, when the current long axis length is larger than the previous long axis length by a middle degree, the output control function 172 generates the image 30 indicating and displays the generated image 30 together with the current ultrasonic image.

Thus, the output control function 172 displays the image indicating the increase/decrease extent of the characteristic amount on the display 13. FIG. 3 is merely an example. For example, the output control function 172 is not limited to output the increase/decrease information in the form of the image 30 and may output the increase/decrease information in other output forms. Other output form by the output control function 172 will be described later.

The storage function 173 is a function that is implemented when the processing circuitry 170 reads a computer program corresponding to the storage function 173 from the storage circuitry 160 and executes it. The storage function 173 stores pieces of ultrasonic image data for the predetermined number of heartbeats specified by the operator in the storage circuitry 160. For example, when the storage function 173 receives press of a save button from the operator, it stores an ultrasonic image data group for the predetermined number of heartbeats (for example, one heartbeat) that contains the currently displayed ultrasonic image data in the storage circuitry 160. The storage function 173 may store the corresponding long axis length information in the storage circuitry 160 together with the ultrasonic image data. It should be noted that any desired number of heartbeats can be set previously as the above-mentioned predetermined number of heartbeats. The storage function 173 is an example of a storage module.

Figure 4:
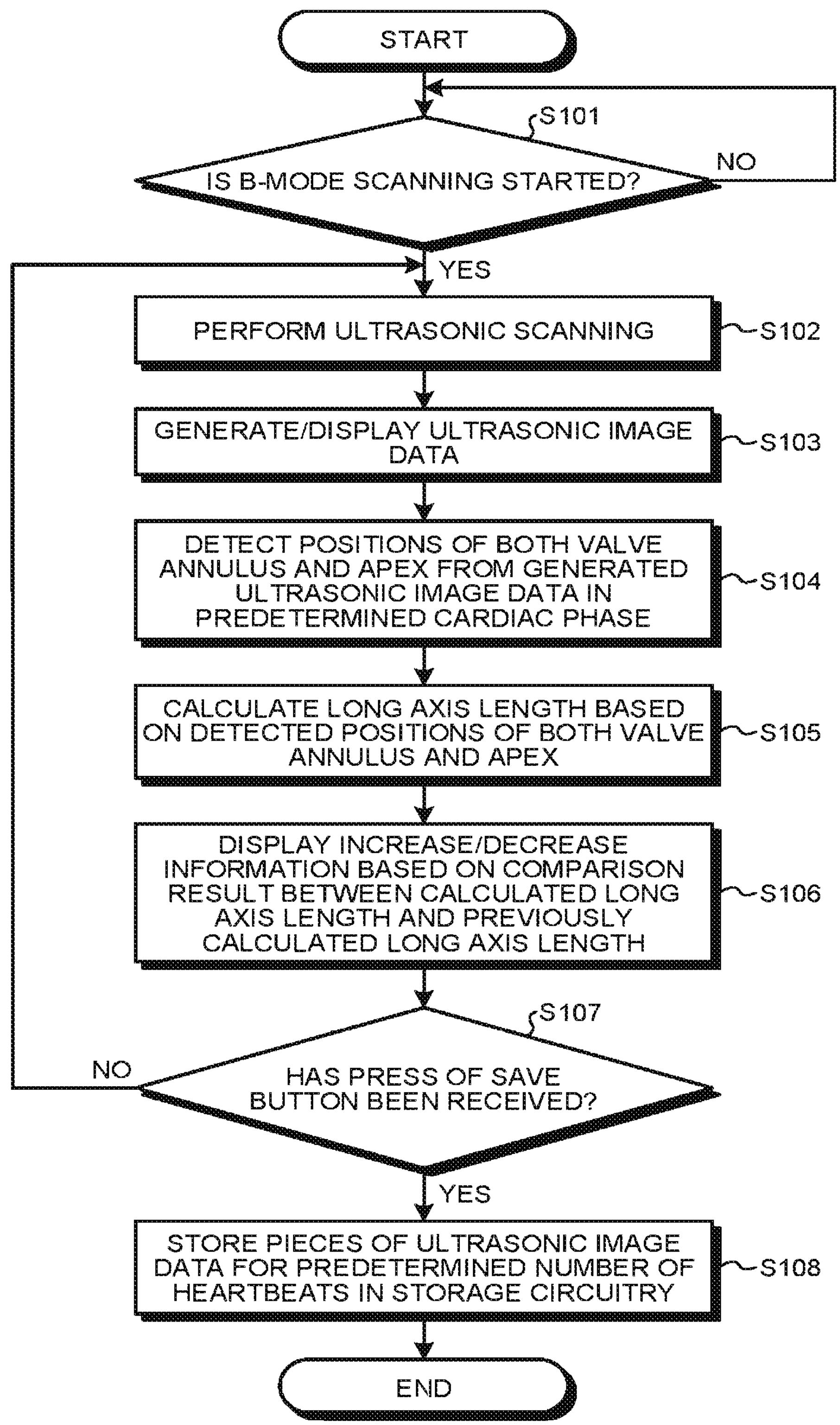
FIG. 4 is an exemplary flowchart illustrating processing procedures the ultrasonic diagnostic apparatus in the first embodiment.

FIG. 4 is a flowchart illustrating processing procedures by the ultrasonic diagnostic apparatus 1 in the first embodiment. For example, the processing procedures as illustrated in FIG. 4 are started when an instruction to start B-mode scanning is received from the operator in a state where the ultrasonic probe 11 is brought into contact with the body surface of the subject P.

At step S101, the processing circuitry 170 starts the B-mode scanning. For example, upon receiving the instruction to start the B-mode scanning from the operator, the processing circuitry 170 starts the B-mode scanning. When step S101 is negative, the processing circuitry 170 does not start the scanning and is made into a standby state.

When step S101 is positive, at step S102, the ultrasonic probe 11 performs the ultrasonic scanning on the two-dimensional region of the subject P.

At step S103, the image generation circuitry 140 generates ultrasonic image data corresponding to the ultrasonic scanning. The output control function 172 displays an image (ultrasonic image) corresponding to the ultrasonic image data generated by the image generation circuitry 140. The generated ultrasonic image data is stored in the image memory 150.

At step S104, the calculation function 171 detects the positions of both valve annulus and the apex from the generated ultrasonic image data in the predetermined cardiac phase (for example, R-wave time phase) (see FIG. 2). For example, the calculation function 171 detects the positions of both valve annulus and the apex contained in the two-dimensional ultrasonic image data using the knowledge based learning algorithm with the teacher.

At step S105, the calculation function 171 calculates the long axis length based on the detected positions of both valve annulus and the apex (see FIG. 2). For example, the calculation function 171 calculates, as the long axis length, the length of the line segment 24 connecting the position 22 of the apex and the middle point of the line segment 23 connecting both valve annulus.

At step S106, the output control function 172 displays the increase/decrease information based on a comparison result between the calculated long axis length and the previously calculated long axis length (see FIG. 3). For example, the output control function 172 displays an image corresponding to any of "+++", "++", "+", "0", "−", "−−", and "−−−".

At step S107, the storage function 173 determines whether it has received the press of the save button. When the determination at step S107 is negative, the storage function 173 does not perform processing at step S108 and the process returns to the processing at step S102. That is to say, the ultrasonic diagnostic apparatus 1 displays a scanned cross section by the ultrasonic probe 11 substantially real time and displays the increase/decrease extent of the long axis length (long axis length information) on the current ultrasonic image from the previous long axis length at a predetermined cardiac cycle (for example, timing of the R wave). This displaying enables the operator to adjust the position and the angle of the ultrasonic probe 11 while browsing the change of the long axis length information in accordance with the changes of the position and angle of the ultrasonic probe 11. As a result of this, the operator can provide, as the desired cross section, the cross section with the longest long axis accurately.

When the determination at step S107 is positive, at step S108, the storage function 173 stores the pieces of ultrasonic image data for the predetermined number of heartbeats in the storage circuitry 160. Then, the ultrasonic diagnostic apparatus 1 finishes the process e Thereafter, the processing circuitry 170 performs analysis of a volume value by the modified Simpson method, the disk summation method, the area length method, and the like on the pieces of ultrasonic image data stored in the storage circuitry 160 so as to perform the cardiac function evaluation based on an instruction from the operator.

FIG. 4 is merely an example. For example, the above-mentioned processing procedures may not be necessarily executed in the above-mentioned order. For example, step S101 to S108 as described above may be executed while the order thereof changed appropriately in a range of consistent processing contents.

As described above, the ultrasonic diagnostic apparatus 1 in the first embodiment, the ultrasonic probe 11 performs the ultrasonic scanning on the two-dimensional region of the subject P. The image generation circuitry 140 functioning as the image generator generates the ultrasonic image data corresponding to the two-dimensional region. The calculation function 171 functioning as the calculator calculates a characteristic amount of the structure that is detected from each of the pieces of ultrasonic image data generated by the ultrasonic scanning at different timings. The output control function 172 functioning as the output controller outputs the information based on the comparison result of the characteristic amounts calculated by the calculation function 171. The ultrasonic diagnostic apparatus 1 can therefore provide the desired cross section accurately.

For example, in the conventional ultrasonic diagnostic apparatus, it has been difficult for the operator to determine whether the long axis length of a cross section that is displayed is larger than those of other cross sections by browsing a two-dimensional ultrasonic image simply. By contrast, the ultrasonic diagnostic apparatus 1 in the first embodiment displays the long axis length information indicating the increase/decrease extent of the long axis length in the current ultrasonic image from the previous long axis length. With this display, the operator can adjust the position and the angle of the ultrasonic probe 11 while browsing change of the long axis length information accordance the changes of the position and the angle of the ultrasonic probe 11. For example, the operator changes the angle of the ultrasonic probe 11 in predetermined direction repeatedly so as to provide a cross section having the longest long axis in the direction. As a result, the operator can provide the cross section passing through the apex accurately as the desired cross section. Furthermore, the ultrasonic diagnostic apparatus 1 can provide the cross section passing through the apex accurately so as to calculate the indicators such as the EF and the GLS that are calculated based on the cross section with high accuracy.

In other words, the operator acquires ultrasonic images of cross sections at different positions by changing the position of the ultrasonic scanning in the ultrasonic scanning at the different timings. Then, the operator compares the long axis lengths that are calculated from the cross sections for the cross sections at the different positions, thereby providing the cross section having the longest long axis. That is to say, in the ultrasonic diagnostic apparatus 1 in the first embodiment, the calculation function 171 calculates the characteristic amounts of the structure that are detected from the pieces of ultrasonic image data generated by the ultrasonic scanning at the different positions. The output control function 172 as the output controller outputs the information based on the comparison result of the characteristic amounts calculated by the calculation function 171. As a result, the ultrasonic diagnostic apparatus 1 can provide the desired cross section.

For example, the ultrasonic diagnostic apparatus 1 displays the long axis length information so as to enable image capturing of the cross sections independent of subjectivity of the operator to be performed. The ultrasonic diagnostic apparatus 1 can therefore provide the cross section identical to that that has been image-captured in the past accurately even when the same operator does not always perform the test (image capturing), for example, thereby improving reproducibility in the follow-up for a long period of time. For example, the ultrasonic diagnostic apparatus 1 can provide the desired cross section accurately without requiring an expensive apparatus configuration.

First Modification of First Embodiment

Although the long axis length information, which is the increase/decrease information, is displayed as the image 30 in the above-mentioned first embodiment, embodiments are not limited thereto. Another output form by the output control function 172 will be described.

Figure 5:
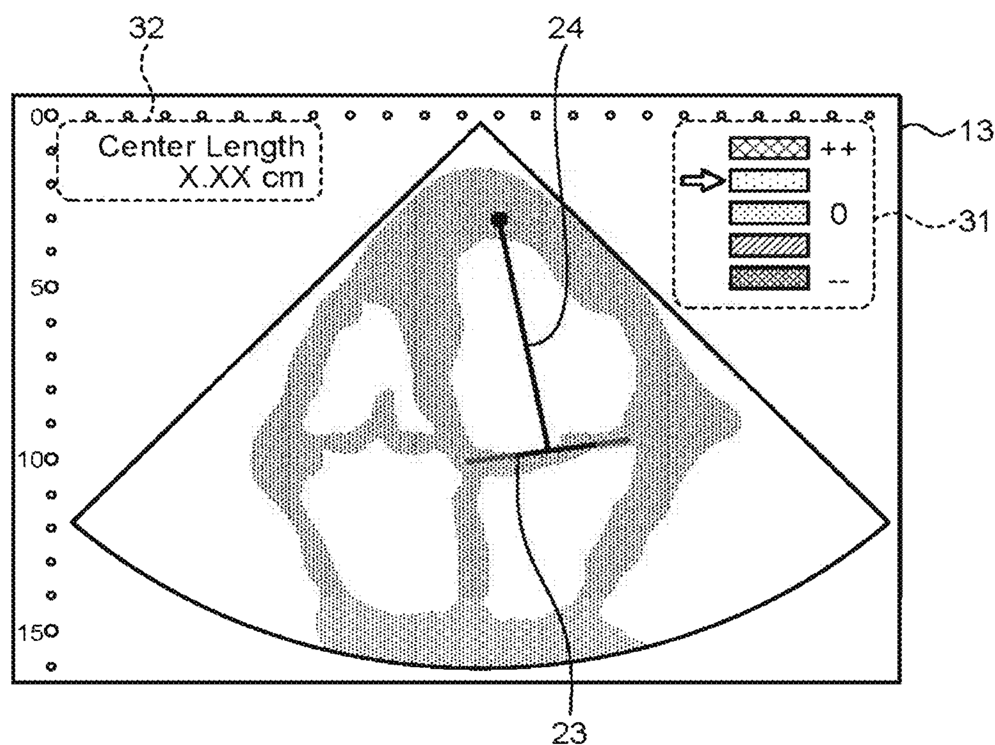
FIG. 5 is an exemplary view for explaining processing of an output control function according to a modification of the first embodiment.

FIG. 5 is a view for explaining processing of the output control function 172 in a modification of the first embodiment. As illustrated in FIG. 5, the output control function 172 can output the long axis length information in another output form.

For example, the output control function 172 displays the long axis length information as an arrow on an indicator 31. The indicator 31 indicates a change amount of the current long axis length from the previous long axis length by five stages of "++", "+", "0", "−", and "−−". That is to say, "++" and "+" indicate that the long axis length calculated at the current timing is larger than the long axis length calculated at the previous timing and as the number of "+" is larger, a difference from the long axis length calculated at the previous timing is larger (that is, the long axis length calculated at the current timing is larger). "−−" and "−" indicate that the long axis length calculated at the current timing is smaller than the long axis length calculated at the previous timing and as the number of "−" is larger, a difference from the long axis length calculated at the previous timing is larger (that is, the long axis length calculated at the current timing is smaller). "0" indicates that the long axis length calculated at the current timing is equivalent to the long axis length calculated at the previous timing. In the example of FIG. 5, the output control function 172 indicates a position of "+" on the indicator 31 by an arrow. This indication enables the operator to recognize the increase/decrease extent of the long axis length based on the position of the arrow on the indicator 31.

For example, the output control function 172 displays the long axis length as numerical value information 32. "Center Length" indicates the long axis length and "X.XX cm" is information indicating a numerical value of the long axis length. To be specific, the output control function 172 displays a numerical value of the long axis length, for example, "8.50 cm", on the display screen of the display 13. This display enables the operator to recognize the current long axis length as the numerical value accurately. The output control function 172 is not limited to display it and may display a change amount ("+0.30 cm", "−0.20 cm", or the like) of the current long axis length from the previous long axis length, for example.

For example, the output control function 172 may display the line segments 23 and 24 as described with reference to FIG. 2 as images. This display enables the operator to recognize the current long axis length intuitively.

In addition to the output forms as illustrated in the FIG. 5, for example, the output control function 172 may output the long axis length information as sound. As an example, the increase of the long axis length and the decrease of the long axis length are expressed by different tones and the increase/decrease extent is expressed by an intensity of the sound. In this case, the output control function 172 outputs the sound with a tone corresponding to the increase or decrease of the long axis length and with an intensity in accordance with the increase/decrease extent of the long axis length.

Alternatively, for example, the output control function 172 may output the long axis length information as vibration. As an example, piezoelectric elements are arranged on a portion of an exterior of the ultrasonic probe 11 that is gripped by the operator. The output control function 172 controls the piezoelectric elements to vibrate in a vibration pattern corresponding to the increase or decrease of the long axis length. In this case, the output control function 172 changes the intensity of the vibration in accordance with the increase/decrease extent of the long axis length.

Second Modification of First Embodiment

Although the long axis length is used as the indicator value (characteristic amount) for determining whether the cross section passes through the apex in the above-mentioned first embodiment, embodiments are not limited thereto. For example, the ultrasonic diagnostic apparatus 1 may use a curvature of a contour in the vicinity of the apex in addition to the long axis length of the left ventricle. The curvature takes a maximum value on the cross section passing through the apex (a cross section with the sharpest contour of the apex is considered to be the accurate cross section).

In this case, for example, the calculation function 171 extracts the contour in the vicinity of the apex (upper end portion of the heart in FIG. 2) from the ultrasonic image data. The calculation function 171 calculates a curvature of the extracted contour.

Then, the output control function 172 compares the current curvature and the previous curvature and provides curvature information as information indicating an increase/decrease extent of the current curvature from the previous curvature. The output control function 172 calculates a composite indicator value obtained by combining the long axis length information and the curvature information so as to use it as the indicator for determining whether the cross section passes through the apex. For example, the composite indicator value is calculated by the following equation. $\alpha$ is a weight coefficient and is 0.6 to 0.7, for example.

$$\text{Composite indicator value} = \alpha \times \text{long axis length information} + (1-\alpha) \times \text{curvature information}$$

Second Embodiment

In the first embodiment, the ultrasonic diagnostic apparatus 1 displays the ultrasonic image substantially real time and displays the increase/decrease extent of the current long axis length from the previous long axis length at the predetermined cardiac cycle. Embodiments are not, however, limited thereto. For example, the ultrasonic diagnostic apparatus 1 may display three or more cross sections that have been image-captured at different timings.

The ultrasonic diagnostic apparatus 1 according to a second embodiment comprises the same configuration as that of the ultrasonic diagnostic apparatus 1 as illustrated in FIG. 1 other than a part of pieces of processing of the output control function 172 and the storage function 173. In the second embodiment, points different from the first embodiment are mainly described and description of points of the same functions as those of the configurations as described in the first embodiment is omitted.

The storage function 173 in the second embodiment stores the pieces of ultrasonic image data for the predetermined number of heartbeats in the image memory 150 every time it receives the press of the save button. For example, the storage function 173 receives the press of the save button from the operator by a plurality of number of times. To be specific, when the operator brings the ultrasonic probe 11 into contact with the subject P and presses the save button (first press), the storage function 173 stores the ultrasonic image data group for at least equal to or more than one heartbeat (one heartbeat in a typical example, the same holds true hereinafter) that contains the ultrasonic image data displayed at this time in a predetermined storage region in the image memory 150. Subsequently, when the operator slightly changes the position and the angle of the ultrasonic probe 11 and presses the save button again (second press), the storage function 173 stores the ultrasonic image data group for at least equal to or more than one heartbeat that contains the ultrasonic image data displayed at this time in the predetermined storage region the image memory 150.

The output control function 172 in the second embodiment simultaneously displays images corresponding to at least three pieces of ultrasonic image data among the pieces of ultrasonic image data that have been image-captured at different timings.

Figure 6:
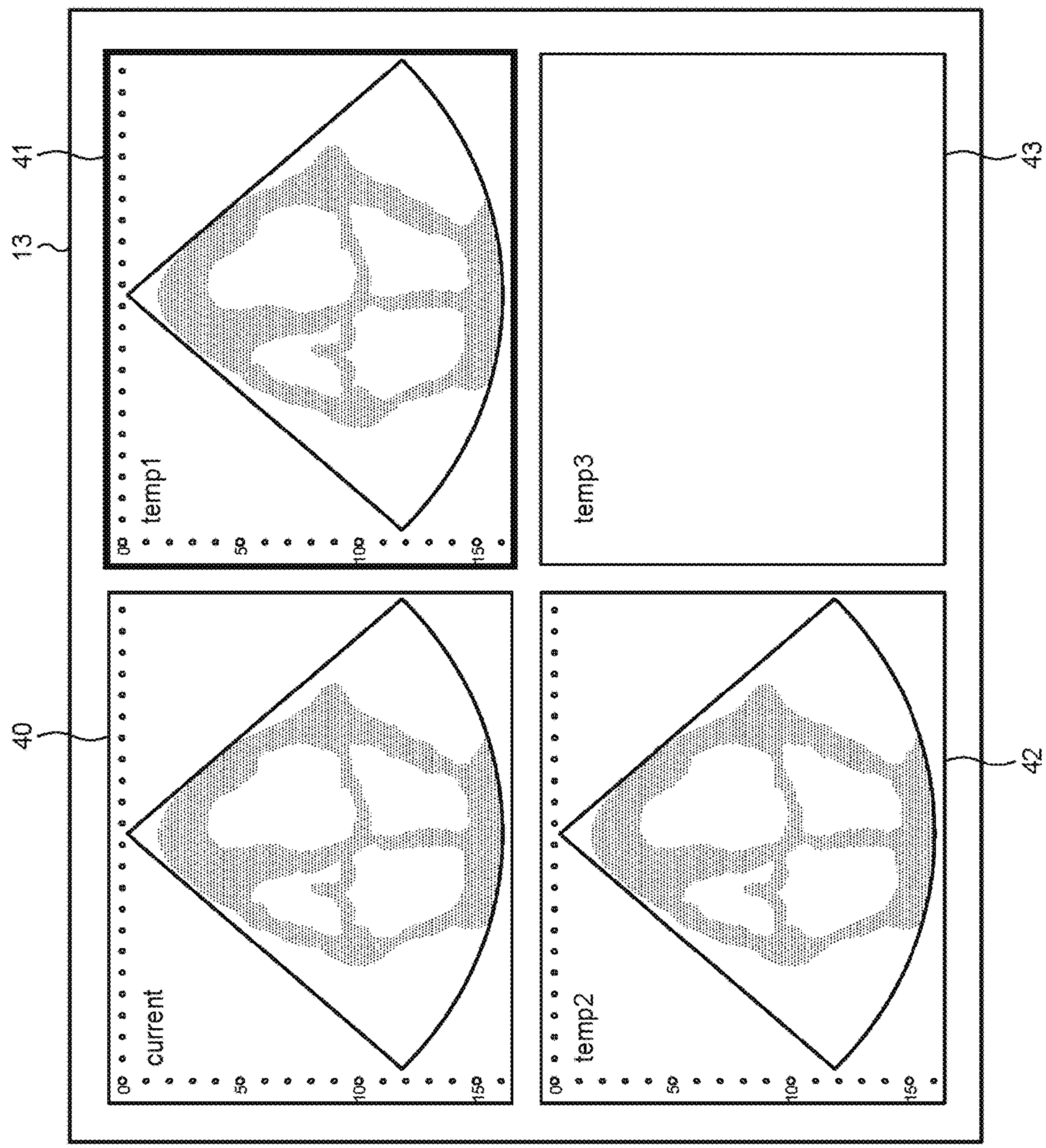
FIG. 6 is an exemplary view for explaining processing of an output control function according to a second embodiment.

FIG. 6 is a view for explaining processing of the output control function 172 in the second embodiment. In FIG. 6, the display screen of the display 13 has four display regions (display regions 40 to 43) for displaying the ultrasonic images. The display regions 40 to 43 are regions for displaying the ultrasonic images that have been image-captured at different timings. For example, the display region 40 is a region for displaying the current ultrasonic image (current image) and the display regions 41 to 43 are regions for repeatedly displaying the ultrasonic images (temp1 image, temp2 image, and temp3 image) at timings at which the ultrasonic images are stored based on instructions from the operator. The temp1 image corresponds to the ultrasonic image data group stored by the first press of the save button, and the temp2 image corresponds to the ultrasonic image data group stored by the second press of the save button. In an example as illustrated in FIG. 6, although no ultrasonic image is displayed on the display region 43, if there is an ultrasonic image data group stored based on an instruction from the operator, it may be displayed on the display region 43.

For example, as illustrated in FIG. 6, upon receiving press of a parallel display button, the output control function 172 displays the current image on the display region 40 and displays the temp1 image and the temp2 image on the display regions 41 and 42, respectively. Each of the temp1 image and the temp2 image is the ultrasonic image data group for one heartbeat, for example. The output control function 172 continuously displays a plurality of ultrasonic images contained in one heartbeat in accordance with the cardiac cycle on each of the display regions 41 and 42 (video display).

Thus, the output control function 172 displays the current ultrasonic image on the display region 40 substantially real time and display the ultrasonic images stored based on instructions from the operator on the display regions 41 to 43.

The output control function 172 synthesizes the cardiac cycles of the images displayed simultaneously based on the electrocardiogram signals detected from the subject P. For example, the output control function 172 sequentially displays the ultrasonic images (temp1 image and temp2 image) corresponding to the electrocardiograms acquired from the electrocardiograph 14 on the display regions 41 and 42. In this manner, the output control function 172 synthesizes the timings of the ultrasonic images that are displayed on the display regions 41 and 42 with the current image.

The output control function 172 highlights an image having the maximum characteristic amount among the images that are displayed simultaneously. For example, the output control function 172 compares the long axis lengths that are calculated from the pieces of ultrasonic image data for the pieces of ultrasonic image data in the R-wave time phase on the display regions 40 to 42. Then, for example, when the long axis length of the ultrasonic image on the display region 41 is the largest, the output control function 172 highlights the ultrasonic image on the display region 41. In the example of FIG. 6, the output control function 172 highlights the ultrasonic image by making a frame surrounding the display region 41 thick.

FIG. 7 is a flowchart illustrating processing procedures by the ultrasonic diagnostic apparatus 1 in the second embodiment. For example, the processing procedures as illustrated in FIG. 7 are started when an instruction to start B-mode scanning is received from the operator in a state where the ultrasonic probe 11 is brought into contact with the body surface of the subject P. Pieces of processing at step S201 to S203 are identical to those at step S101 to S103 as illustrated in FIG. 4 and description thereof is omitted.

At step S204, the storage function 173 determines whether it has received the press of the save button. When the determination at S204 is negative, the storage function 173 does not perform processing at step S205 and the process returns to the processing at step S202. That is to say, the ultrasonic diagnostic apparatus 1 displays the ultrasonic image substantially real time.

When the determination at step S204 is positive, at step S205, the storage function 173 stores the pieces of ultrasonic image data for the predetermined number of heartbeats (for example, one heartbeat) in the predetermined storage region in the image memory 150.

At step S206, the calculation function 171 detects the positions of both valve annulus and the apex from the generated ultrasonic image data in the predetermined cardiac phase (for example, R-wave time phase). For example, the calculation function 171 detects the positions of both valve annulus and the apex contained in the two-dimensional ultrasonic image data using the knowledge based learning algorithm with the teacher.

At step S207, the calculation function 171 calculates the long axis length based on the detected positions of both valve annul us and the apex. For example, the calculation function 171 calculates, as the long axis length, the length of the line segment 24 connecting the position 22 of the apex and the middle point of the line segment 23 connecting both valve annulus.

At step S208, the output control function 172 determines whether it has received press of the parallel display button. When the determination at step S208 is negative, the output control function 172 does not perform processing at step S209 and the process returns to the processing at step S202. That is to say, the ultrasonic diagnostic apparatus 1 receives the press of the save button repeatedly while displaying the ultrasonic image substantially real time.

When the determination at step S208 is positive, at step S209, the output control function 172 displays the pieces of stored ultrasonic image data in parallel and highlight the ultrasonic image data having the largest long axis length (see FIG. 6). For example, the current ultrasonic image (current image) is displayed on the display region 40 substantially real time whereas the ultrasonic images (temp1 image, temp2 image, and temp3 image) stored based on the instructions from the operator are displayed on the display regions 41 to 43.

At step S210, the storage function 173 determines whether any of the ultrasonic images has been selected. For example, the storage function 173 determines whether any of the ultrasonic images among the current image, the temp1 image, and the temp2 image as illustrated in FIG. 6 has been selected. When the determination at step S210 is negative, the storage function 173 does not perform processing at step S211 and is made into a standby state.

When the determination at step S210 is positive, at step S211, the storage function 173 stores the pieces of selected ultrasonic image data for the predetermined number of heartbeats (for example, one heartbeat) in the storage circuitry 160.

FIG. 7 is merely an example. For example, the above-mentioned processing procedures may not be necessarily executed in the above-mentioned order. For example, the processing at step S208 may not be necessarily executed. That is to say, the output control function 172 may perform the processing at step S209 even when it does not necessarily receive the press of the parallel display button. In this case, the output control function 172 sequentially displays the pieces of stored ultrasonic image data as the temp1 image, the temp2 image, and the temp3 image every time the storage function 173 stores the pieces of ultrasonic image data in the image memory 150. Then, the output control function 172 compares the long axis lengths of the ultrasonic images that are stored in the image memory 150 and highlights the ultrasonic image having the maximum long axis length.

As described above, the ultrasonic diagnostic apparatus 1 in the second embodiment simultaneously displays three or more cross sections that have been image-captured at different timings. The ultrasonic diagnostic apparatus 1 enables the operator to specify the cross section having the peak long axis length by simply browsing the screen on which three or more cross sections, at different positions provided by slightly changing a manner in which the probe touches the subject P, are displayed simultaneously. In other words, if only two cross sections are displayed, the operator can recognize the magnitude relation between the long axis lengths thereof but cannot recognize the cross section having the peak long axis length. The ultrasonic diagnostic apparatus 1 in the second embodiment displays three or more cross sections simultaneously so as to enable the operator to specify the cross section having the largest long axis length among candidates of the cross sections with different manners of the probe touching the subject. The ultrasonic diagnostic apparatus 1 can therefore provide the desired cross section accurately.

In other words, the operator changes the positions of the ultrasonic scanning in the ultrasonic scanning at different timings, so that the cross sections at different positions are displayed simultaneously. The operator can specify the cross section having the largest long axis length by simply browsing the cross sections at the different positions that are displayed simultaneously. That is to say, in the ultrasonic diagnostic apparatus 1 in the first embodiment, the calculation function 171 calculates the characteristic amounts of the structure that are detected from the pieces of ultrasonic image data generated by the ultrasonic scanning at different positions. The output control function 172 as the output controller outputs the information based on the comparison result of the characteristic amounts calculated by the calculation function 171. As a result, the ultrasonic diagnostic apparatus 1 can provide the desired cross section.

For example, cross sections are image-captured under various clinical conditions and image quality conditions in clinical practice, and the long axis length of the cross section passing through the apex is not necessarily the largest depending on the conditions. That is, only the long axis length cannot provide the cross section passing through the apex in some cases. As for this point, the ultrasonic diagnostic apparatus 1 in the second embodiment displays the cross sections simultaneously so as to enable the operator to browse the cross sections and select the cross section. With this display, the operator can consider characteristics other than the long axis length, such as a sharpness degree of the apical lumen and a shape of the ventricle, thereby providing the cross section passing through the apex accurately.

Contents as described in the first embodiment can be also applied to the second embodiment except that the cross sections are displayed simultaneously. For example, the output control function 172 may display the image 30 as described in the first embodiment on the current image of FIG. 6.

Third Embodiment

In the above-mentioned first and, second embodiments, the cross section that possibly has the peak long axis length is offered to the operator. Embodiments are not, however, limited thereto. For example, the ultrasonic diagnostic apparatus 1 may notify the operator of the cross section having the long axis length that is not the largest as the cross section (obliquely cut cross section) that does not pass through the apex.

That is to say, in the case where the A4C image and the A2C image are obtained, when both of them are obtained as cross sections passing through the apex, the long axis lengths of them should be identical and are the largest. In other words, when the long axis lengths of them are different, it is known that at least the cross section having the smaller long axis length does not pass through the apex. In consideration of this, the ultrasonic diagnostic apparatus 1 according to a the third embodiment compares the long axis lengths of the A4C image and the A2C image when they are obtained and notifies the operator of the cross section having the smaller long axis length so as to notify the operator of the cross section that does not pass through the apex.

The ultrasonic diagnostic apparatus 1 in the third embodiment comprises the same configuration as that of the ultrasonic diagnostic apparatus 1 as illustrated in FIG. 1 other than a part of pieces of processing of the calculation function 171, the output control function 172, and the storage function 173. In the third embodiment, points different from the first embodiment are mainly described and description of points of the same functions as those of the configurations as described in the first embodiment is omitted. In the third embodiment, although a 1D array probe is applied as the ultrasonic probe 11, a 2D array probe may be applied.

The storage function 173 in the third embodiment stores pieces of ultrasonic data of the A4C image and the A2C image in the image memory 150. For example, the operator moves the ultrasonic probe 11 to a position at which the A4C image can be considered to be provided and inputs an instruction to start scanning the A4C image (presses the button and so on). With this operation, the storage function 173 stores pieces of ultrasonic image data of the A4C image in the image memory 150. For example, the storage function 173 stores, as an ultrasonic image data group of the A4C image, an ultrasonic image data group for one heartbeat that contains the ultrasonic image data displayed at the time point at which the instruction has been input in a predetermined storage region in the image memory 150.

For example, the operator moves the ultrasonic probe 11 to a position at which the A2C image can be considered to be provided and inputs an instruction to start scanning the A2C image. With this operation, the storage function 173 stores pieces of ultrasonic image data of the A2C image in the image memory 150. For example, the storage function 173 stores, as an ultrasonic image data group of the A2C image, an ultrasonic image data group for one heartbeat that contains the ultrasonic image data displayed at the time point at which the instruction has been input in the predetermined storage region in the image memory 150.

Thus, the storage function 173 stores the pieces of ultrasonic image data of the A4C image and the A2C image in the image memory 150. It should be noted that the operator can also start scanning the A4C image and the A2C image again. In this case, the storage function 173 updates the pieces of ultrasonic image data stored in the predetermined storage region in the image memory 150 by new pieces of ultrasonic image data.

The calculation function 171 in the third embodiment calculates the long axis lengths for the pieces of the ultrasonic image data of the A4C image and the A2C image. For example, when the storage function 173 stores the pieces of ultrasonic image data of the A4C image in the predetermined storage region in the image memory 150, the calculation function 171 detects the positions of both valve annulus and the ape from ultrasonic image data in the R-wave time phase among the pieces of stored ultrasonic image data. Then, the calculation function 171 calculates the long axis length based on the detected positions of both valve annulus and the apex. The calculation function 171 calculates the long axis length for the pieces of ultrasonic image data of the A2C image in the same manner.

The output control function 172 in the third embodiment highlights the A4C image or the A2C image having the smaller long axis length.

Figure 8:
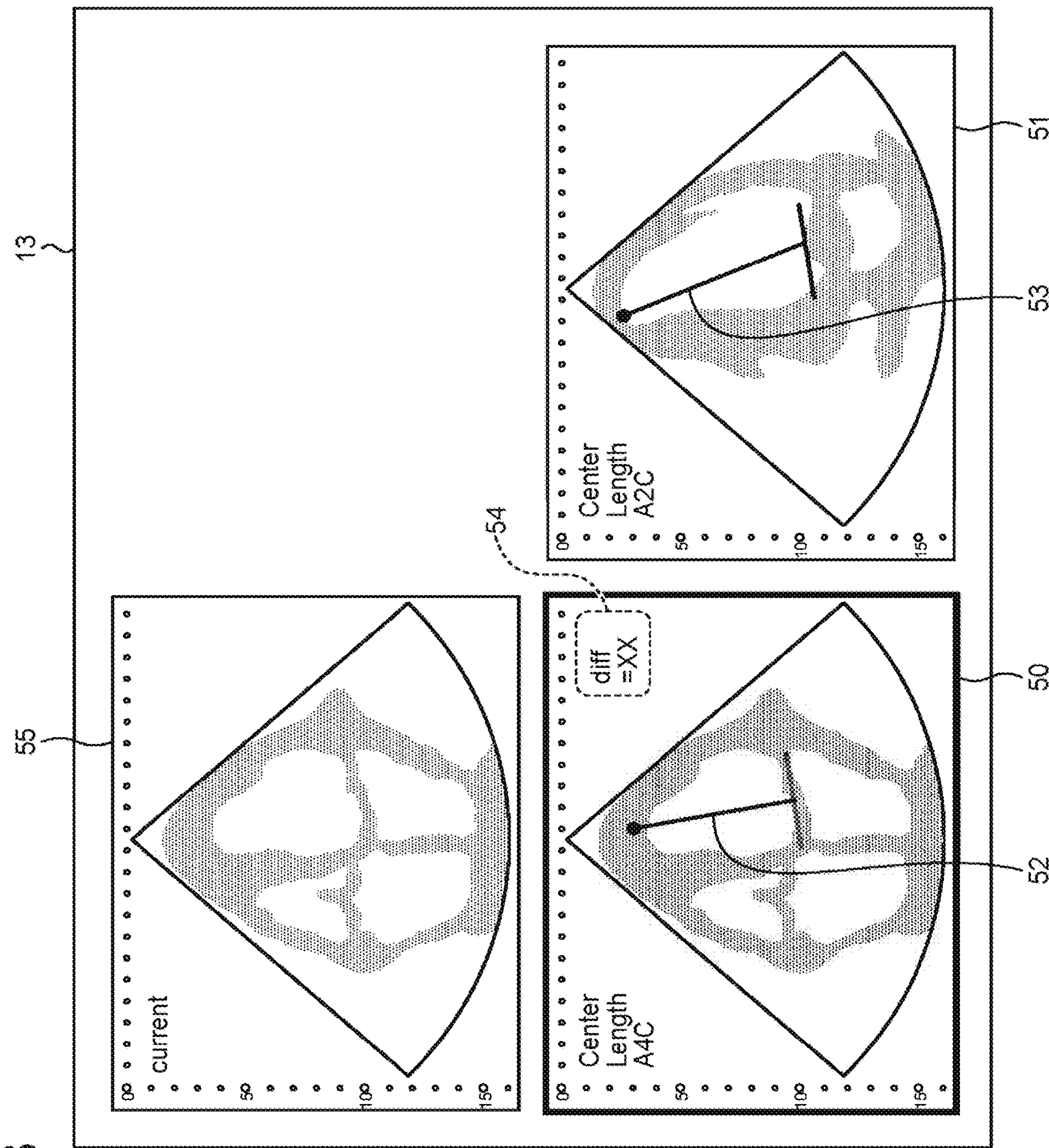
FIG. 8 is an exemplary view for explaining processing of an output control function according to a third embodiment.

FIG. 8 is a view for explaining processing of the output control function 172 in the third embodiment. In FIG. 8, the display screen of the display 13 contains a display region 50 for displaying the A4C image, a display region 51 for displaying the A2C image, and a display region 55 for displaying the current image. When the operator starts scanning the A4C image and the A2C image, the operator operates the ultrasonic probe 11 while browsing the current image and presses a scanning button. With this operation, the operator starts scanning the A4C image that is displayed on the display region 50 and the A2C image that is displayed on the display region 51.

As illustrated in FIG. 8, the output control function 172 compares the long axis images of the A4C image and the A2C image that the calculation function 171 have calculated. For example, when the long axis length of the A4C image is smaller than the long axis length of the A2C image, the output control function 172 highlights the A4C image. In the example of FIG. 8, the output control function 172 highlights the A4C image by making a frame surrounding the display region 50 thick.

For example, the output control function 172 displays, as images, line segments 52 and 53 indicating the mal or axes that are calculated by the calculation function 171. The line segment 52 is an image of the long axis on the A4C image and the line segment 53 is an image of the long axis on the A2C image. This display enables the operator to recognize the long axis lengths of the A4C image and the A2C image intuitively based on the lengths of the line segments.

For example, the output control function 172 displays, as numerical value information 54, a differential value between the long axis lengths of the A4C image and the A2C. "Diff" indicates a differential value and "=XX" is information indicating the differential value by a numerical value. To be specific, the output control function 172 displays the differential value, for example, "0.22 cm", on the display screen of the display 13. This display enables the operator to recognize the current long axis length as the numerical value accurately.

Figure 9:
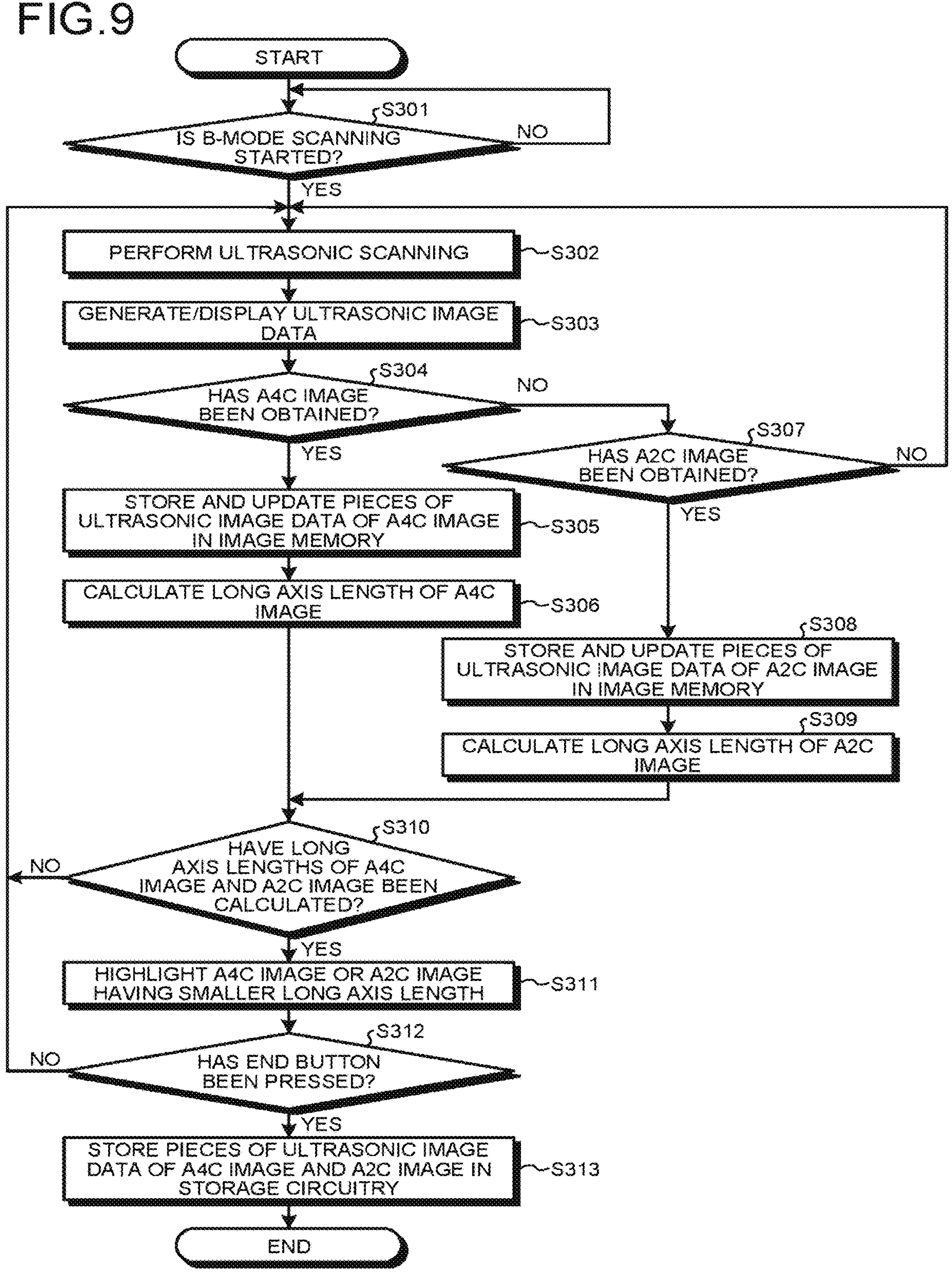
FIG. 9 is an exemplary flowchart illustrating processing procedures by an ultrasonic diagnostic apparatus in the third embodiment.

FIG. 9 is a flowchart illustrating processing procedures by the ultrasonic diagnostic apparatus 1 in the third embodiment. For example, the processing procedures as illustrated in FIG. 9 are started when an instruction to start B-mode scanning is received from the operator in a state where the ultrasonic probe 11 is brought into contact with the body surface of the subject P. Pieces of processing at steps S301 to S303 are identical to those at step S101 to S103 as illustrated in FIG. 4 and description thereof is omitted.

At step S304, the storage function 173 determines whether it has received an instruction to start scanning the A4C image. For example, the operator moves the ultrasonic probe 11 to a position at which the A4C image can be considered to be provided and inputs the instruction to start scanning the A4C image. With this operation, the storage function 173 receives the instruction to start scanning the A4C image from the operator. When the determination at step S304 is negative, the storage function 173 proceeds to step S307.

When the determination at step S304 is positive, at step S305, the storage function 173 stores the pieces of ultrasonic image data of the A4C image in the image memory 150. For example, the storage function 173 stores the pieces of ultrasonic image data for the predetermined number of heartbeats (for example, one heartbeat) for the A4C in the predetermined storage region in the image memory 150. In this case, the output control function 172 displays the A4C image on a predetermined display region on the display 13 based on the pieces of stored ultrasonic image data. When the A4C image is obtained again, the storage function 173 updates the pieces of ultrasonic image data stored in the predetermined storage region in the image memory 150 by new pieces of ultrasonic image data.

At step S306, the calculation function 171 calculates the long axis length of the A4C image. For example, the calculation function 171 detects the positions of both valve annulus and the apex from the A4C image, and calculates the long axis length based on the detected positions or both valve annulus and the apex.

At step S307, the storage function 173 determines whether it has received the instruction to start scanning the A2C image. For example, the operator moves the ultrasonic probe 11 to a position at which the A2C image can be considered to be provided and inputs the instruction to start scanning the A2C image. With this operation, the storage function 173 receives the instruction to start scanning the A2C image from the operator. When the determination at step S307 is negative, the storage function 173 returns the process to step S302.

When the determination at step S307 is positive, at step S308, the storage function 173 stores pieces of ultrasonic image data of the A2C image in the image memory 150. For example, the storage function 173 stores the pieces of ultrasonic image data for the predetermined number of heartbeats (for example, one heartbeat) for the A2C in the predetermined storage region in the image memory 150. In this case, the output control function 172 displays the A2C image on the predetermined display region on the display 13 based on the stored pieces of ultrasonic image data. When the A2C image is obtained again, the storage function 173 updates the pieces of ultrasonic image data stored in the predetermined storage region in the image memory 150 by new pieces of ultrasonic image data.

At step S309, the calculation function 171 calculates the long axis length of the A2C image. For example, the calculation function 171 detects the positions of both valve annulus and the apex from the A2C image, and calculates the long axis length based on the detected positions of both valve annulus and the apex.

At step S310, the output control function 172 determines whether the long axis lengths of the A4C image and the A2C image have been calculated. When the determination at step S310 is negative, the process returns to the processing at step S302. That is to say, the ultrasonic diagnostic apparatus 1 executes the pieces of processing at step S302 to S309 repeatedly until the long axis lengths of the A4C image and the A2C image are calculated.

When the determination at step S310 is positive, at step S311, the output control function 172 highlights the A4C image or the A2C image having the smaller long axis length. As illustrated in FIG. 8, for example, when the long axis length of the A4C image is smaller than the long axis length of the A2C image, the output control function 172 highlights the A4C image.

At step S312, the storage function 173 determines whether a scanning end button has been pressed. When the determination at step S312 is negative, the storage function 173 returns the process to the processing at step S302.

That is to say, for the A4C image and the A2C image, the operator can start scanning the A4C image and the A2C image again while changing the position and the angle of the ultrasonic probe 11 with reference to the display screen as illustrated in FIG. 8 until the desired cross section is provided. For example, when any one of the long axis lengths of the A4C image and the A2C image is smaller, the operator changes the position and the angle of the cross section having the smaller long axis length and starts scanning the cross section again.

To be specific, when the long axis length of the A4C image is smaller than the long axis length of the A2C image, the operator changes the position and the angle of the ultrasonic probe 11 for the cross section of the A4C image. It should be noted that the A4C image and the A2C image are deviated from each other by approximately 60 degrees (or 120 degrees) about the long axis. When a cross section (provided by rotating the A4C image by 90 degrees) orthogonal to the A4C image as a reference is extracted as the corresponding A2C image, the operator preferably moves the position of the ultrasonic probe 11 in the direction perpendicular to the cross section (hereinafter, the corresponding A2C image is simply referred to as the A2C image in the third embodiment and a fourth embodiment). Then, the operator starts scanning the A4C image at a position after being moved, again. In this case, the output control function 172 compares the long axis length of the A4C image obtained again and the long axis length of the A2C image and highlights the A4C image or the A2C image having the smaller long axis length.

When the long axis length of the A4C image is larger than the long axis length of the A2C image, the operator then changes the position and the angle of the ultrasonic probe 11 for the cross section of the A2C image. On the other hand, when the long axis length of the A4C image is still smaller than the long axis length of the A2C image, the operator changes the position and the angle of the ultrasonic probe 11 for the cross section of the A4C image, again. When the long axis length of the A4C image is equivalent to the long axis length of the A2C image, the operator determines that both cross sections passing through the apex have been provided.

The long axis lengths of the A4C image and the A2C image that have been initially obtained are equivalent to each other in some cases. In this case, they are considered to be possibly equivalent to each other by accident although the long axis lengths of them are not the largest. Even in this case, the operator preferably performs operations of changing both cross sections and comparing the long axis lengths of them at least once for each.

When the determination at step S312 is positive, at step S313, the storage function 173 stores the pieces of ultrasonic image data of the A4C image and the A2C image in the storage circuitry 160.

FIG. 9 is merely an example. For example, the above-mentioned processing procedures may not be necessarily executed in the above-mentioned order. For example, the pieces of processing of calculating the long axis lengths of the A4C image and the A2C image at steps S306 and S309, respectively, may be executed after the processing at step S301.

Thus, the ultrasonic diagnostic apparatus 1 in the third embodiment starts scanning the A4C image and the A2C image and notifies the operator of the A4C image or the A2C image having the smaller long axis length. This notification enables the operator to know the cross section to be changed and to therefore change the position and the angle of the ultrasonic probe 11 that image-captures the cross section.

Notification of Third Embodiment

In the above-mentioned third embodiment, images that have been obtained in past examination may be displayed simultaneously.

Figure 10:
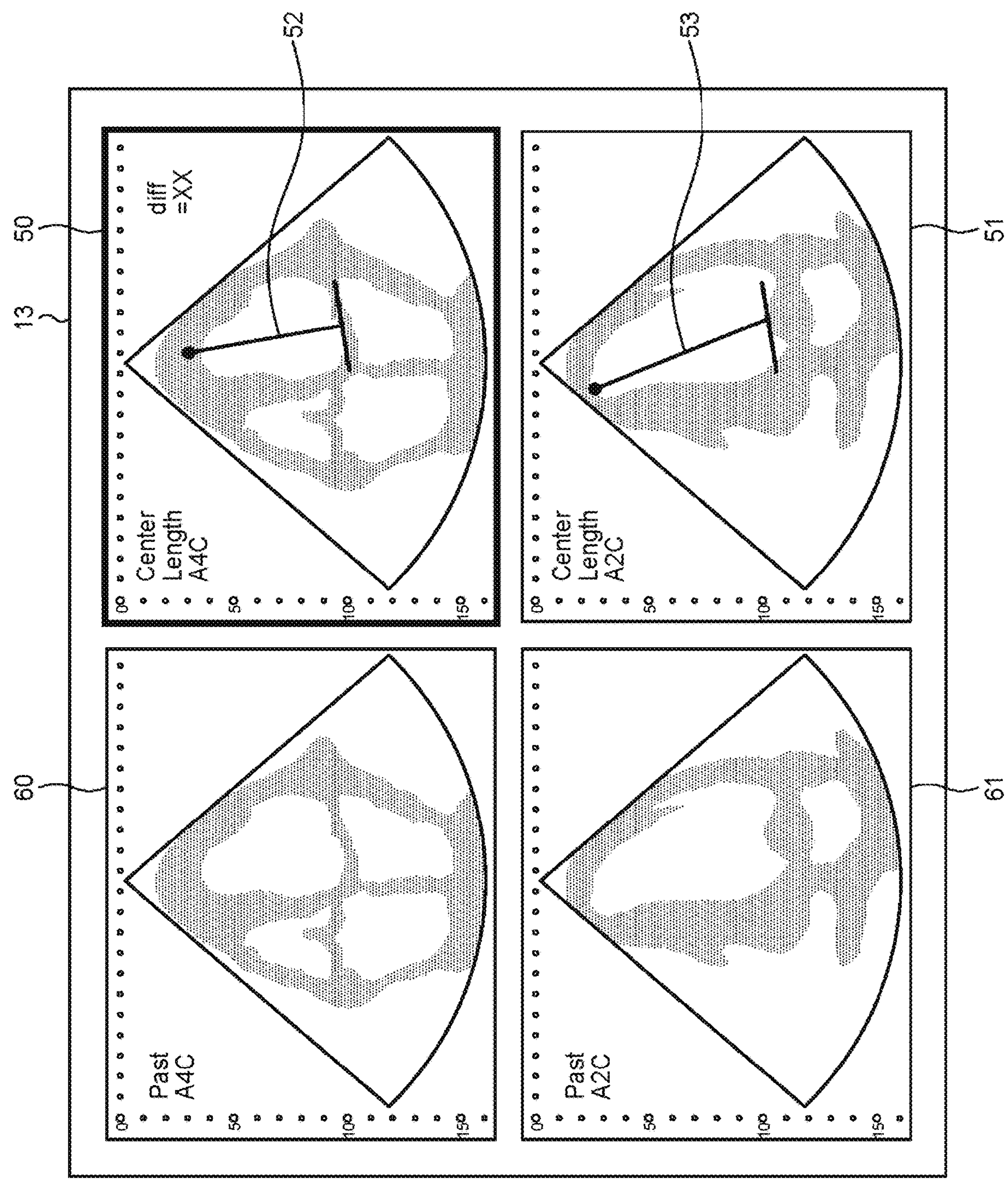
FIG. 10 is an exemplary view for explaining processing of an output control function according to a modification of the third embodiment.

FIG. 10 is a view for explaining processing of the output control function 172 in a modification of the third embodiment. In FIG. 10, the display screen of the display 13 contains the display region 50 for displaying the A4C image in the current examination, the display region 51 for displaying the A2C image in the current examination, a display region 60 for displaying an A4C image in a past examination, and a display region 61 for displaying the A2C image in the past examination.

As illustrated in FIG. 10, the output control function 172 displays the A4C image and the A2C image generated by the image generation circuitry 140 in the current examination on the display regions 50 and 51, respectively, and display the A4C image and the A2C image obtained in the past examination on the display regions 60 and 61, respectively. The images that are displayed on the display regions 50, 51, 60, and 61 may be still images in certain cardiac phases (for example, R-wave time phases) or a plurality of images for the predetermined number of heartbeats (for example, one heartbeat) may be continuously displayed (video-displayed) on the display regions 50, 51, 60, and 61.

For example, when the images for the predetermined number of heartbeats (for example, one heartbeat) are continuously displayed on the display regions 50, 51, 60, and 61, the output control function 172 synthesizes the cardiac cycles of the four images that are displayed simultaneously based on the electrocardiogram signals detected from the subject P. For the A4C image and the A2C image obtained in the past examination, pieces of information indicating timings in the electrocardiograms are given to the stored images. For example, the output control function 172 sequentially displays the images (the A4C image and the A2C image) corresponding to the electrocardiograms acquired from the electrocardiograph 14 on the display regions 50 and 51. Furthermore, the output control function 172 sequentially displays the A4C image and the A2C image obtained in the past examination at timings corresponding to the electrocardiograms of the images that are displayed on the display regions 50 and 51. In this manner, the output control function 172 synthesizes the cardiac cycles of the four images that are displayed simultaneously.

As described above, in the modification of the third embodiment, the ultrasonic diagnostic apparatus 1 displays the images obtained in the current examination and the images obtained in the past examination simultaneously. This display enables the operator to browse the cross sections by the current examination and the cross sections by the past examination in parallel, thereby providing the cross sections identical to the cross sections in the past easily. For example, even when the operator is different between the past examination and the current examination, the operator in the current examination can provide the cross sections identical to the cross sections in the past easily.

The contents as described in the first embodiment and the second embodiment can be also applied to the third embodiment except that the operator is notified of the cross section of the A4C image or the A2C image having the smaller long axis length. For example, the output control function 172 may display the image 30 as described in the first embodiment on the current ultrasonic image that is displayed substantially real time.

Although the 1D array probe is applied as the ultrasonic probe 11 in the above-mentioned third embodiment, a 2D array probe may be applied. When the 2D array probe is applied, for example, the operator can start scanning initial cross sections of the A4C image and the A2C image by one-time operation. Also in this case, the operations of comparing the long axis lengths of the A4C image and the A2C image and changing the cross section having the smaller long axis length are identical to those as described above.

Although the output control function 172 notifies the operator of the cross section having the smaller long axis length in the above-mentioned third embodiment, the output control function 172 may notify the operator of the cross section having the larger long axis length. Also in this case, the above-mentioned operations can be executed because the operator can know the cross section to be changed (the cross section having the smaller long axis length).

Fourth Embodiment

In the above-mentioned first to third embodiments, the operator changes the cross section by being notified of the information as the indicator for determining whether the cross section passing through the apex has been provided. Embodiments are not, however, limited thereto. For example, the ultrasonic diagnostic apparatus 1 may automatically change the cross section and offer an appropriate cross section to the operator.

Figure 11:
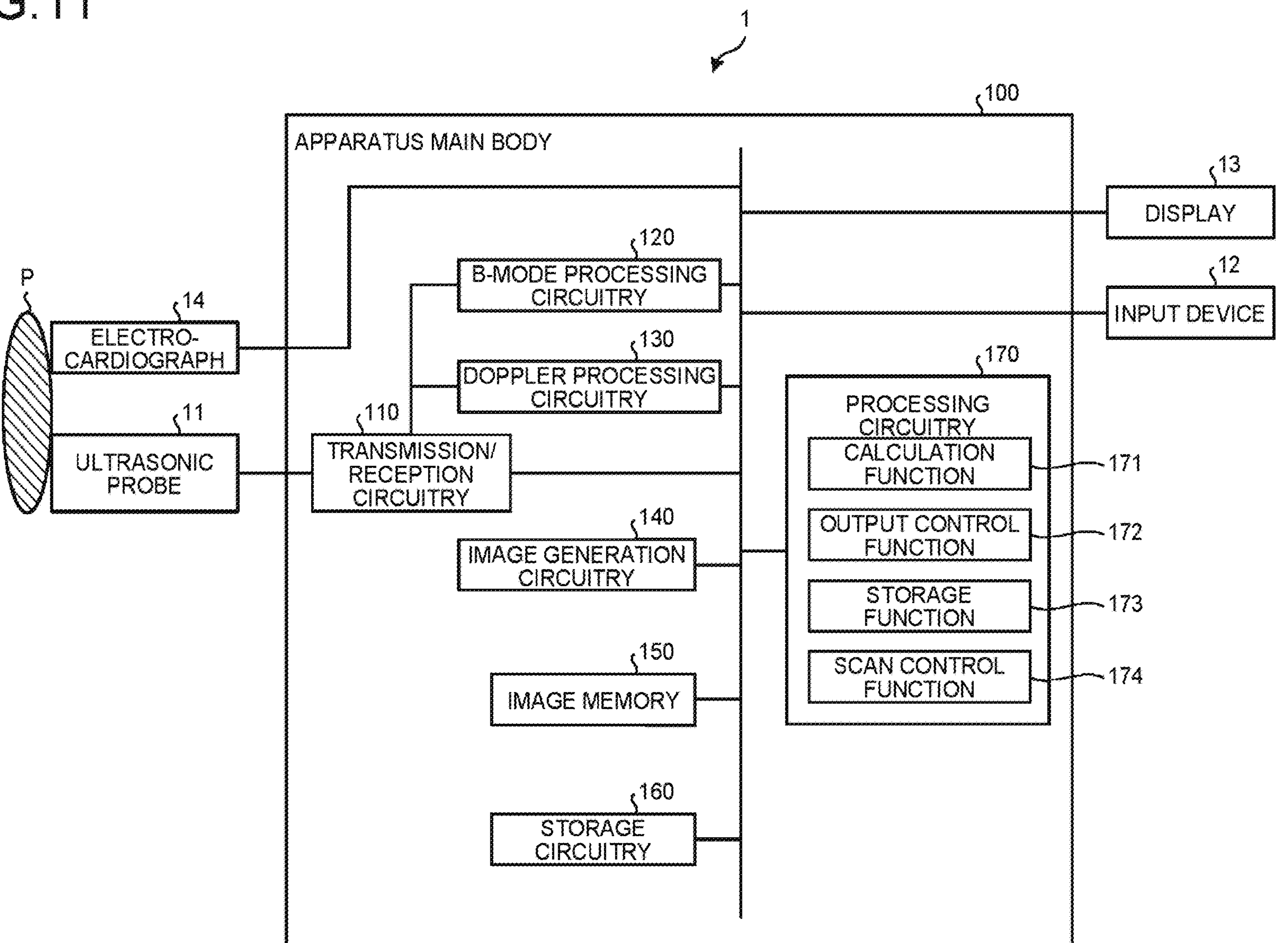
FIG. 11 is an exemplary block diagram illustrating an example of the configuration of an ultrasonic diagnostic apparatus according to a fourth embodiment.

FIG. 11 is a block diagram illustrating an example of the configuration of an ultrasonic diagnostic apparatus according to the fourth embodiment. The ultrasonic diagnostic apparatus 1 in the fourth embodiment comprises the same configuration as that of the ultrasonic diagnostic apparatus 1 as illustrated in FIG. 1 except that the ultrasonic probe 11 is a 2D array probe and the processing circuitry 170 further executes a can control function 174, and a part of pieces of processing of the calculation function 171, the output control function 172, and the storage function 173. In the fourth embodiment, points different from the first embodiment are mainly described and the same reference numeral as those in FIG. 1 denote points of the same functions as those of the configurations as described in the first embodiment and description thereof is omitted.

The scan control function 174 is a function that is implemented when the processing circuitry 170 reads a computer program corresponding to the scan control function 174 from the storage circuitry 160 and executes it. The scan control function 174 causes the ultrasonic probe 11 to perform the ultrasonic scanning in which the positions of the cross sections of the A4C image and the A2C image are changed to decrease the difference between the long axis length of the A4C image and the long axis length of the A2C image. For example, when the long axis length of the A4C image in the long axis lengths of the A4C image and the A2C image is smaller, the scan control function 174 causes the ultrasonic probe 11 to perform the ultrasonic scanning in which the position of the cross section of the A4C image is changed. When the long axis length of the A2C image is smaller, the scan control function 174 causes the ultrasonic probe 11 to perform the ultrasonic scanning in which the position of the cross section of the A2C image is changed. The following describes processing of the scan control function 174 with reference to FIG. 12.

Figure 12:
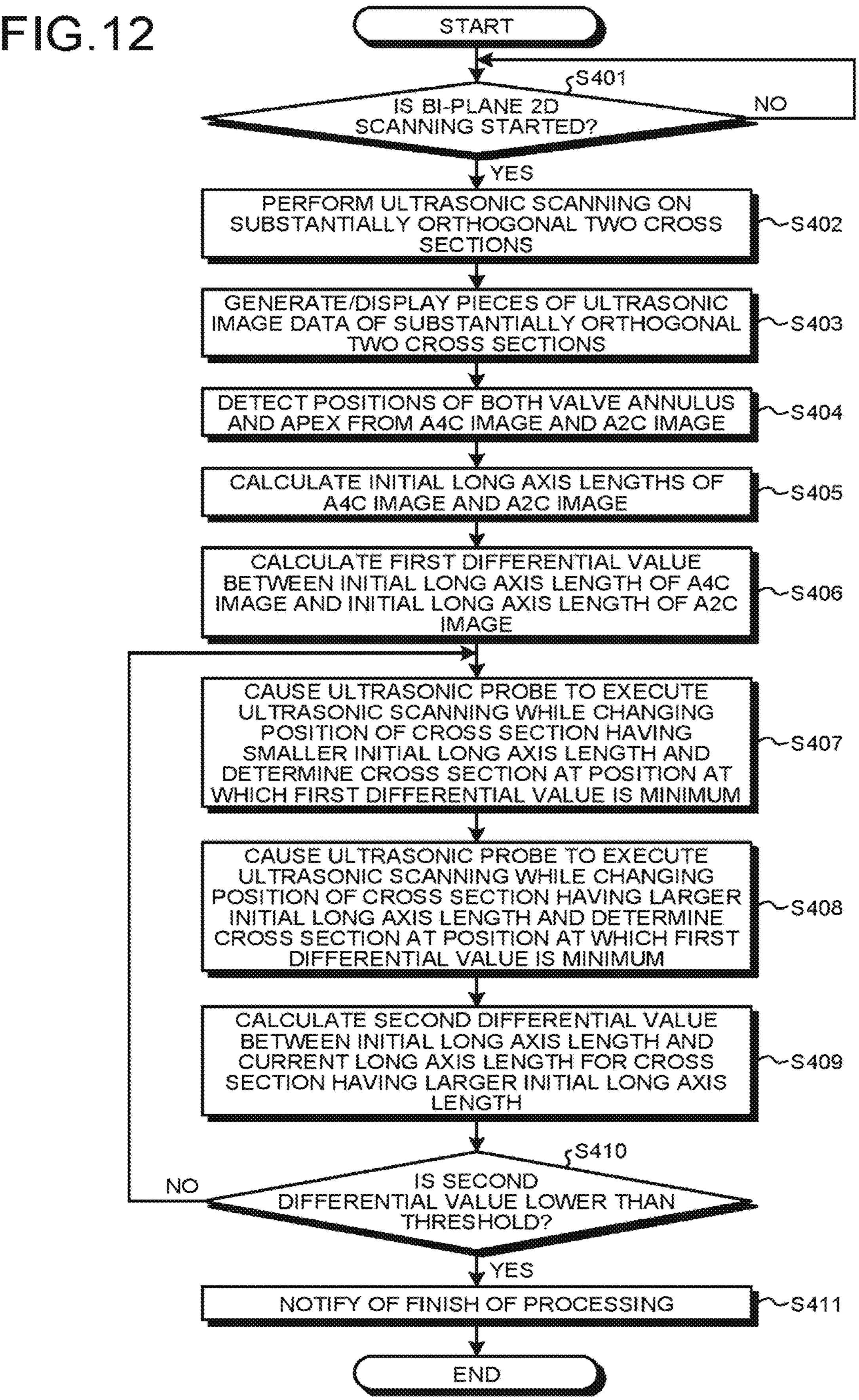
FIG. 12 is an exemplary flowchart illustrating processing procedures by the ultrasonic diagnostic apparatus in the fourth embodiment.

FIG. 12 is a flowchart illustrating processing procedures by the ultrasonic diagnostic apparatus 1 in the fourth embodiment. The processing procedures as illustrated in FIG. 12 are started when an instruction to start bi-plane 2D scanning is received from the operator in a state where the ultrasonic probe 11, which is the 2D array probe, is brought into contact with the body surface of the subject P.

At step S401, the processing circuitry 170 starts the bi-plane 2D scanning. For example, when the processing circuitry 170 receives the instruction to start the bi-plane 2D scanning from the operator, the processing circuitry 170 starts the bi-plane 2D scanning. When step S401 is negative, the processing circuitry 170 does not start the scanning and is made into a standby state.

When step S401 is positive, at step S402, the ultrasonic probe 11 performs the ultrasonic scanning on substantially orthogonal two cross sections.

At step S403, the image generation circuitry 140 generates pieces of ultrasonic image data of the substantially orthogonal two cross sections. Then, the output control function 172 displays a bi-plane 2D image (two ultrasonic images that are substantially orthogonal to each other)

corresponding to the pieces of ultrasonic image data generated by the image generation circuitry 140. The operator changes the position and the angle of the ultrasonic probe 11 such that the displayed bi-plane 2D image will correspond to the A4C image and the A2C image. Then, when the operator determines that the A4C image and the A2C image are provided substantially, the operator holds the position and the angle of the ultrasonic probe 11 and the processing at step S404 and subsequent pieces of processing are started.

At step S404, the calculation function 171 detects the positions of both valve annulus and the apex from each of the A4C image and the A2C image.

At step S405, the calculation function 171 calculates the long axis lengths of the A4C image and the A2C image as initial long axis lengths.

At step S406, the scan control function 174 calculates a first differential value between the initial long axis length of the A4C image and the initial long axis length of the A2C image. The first differential value is an absolute value of the difference between the initial long axis length of the A4C image and the initial long axis length of the A2C image.

At step S407, the scan control function 174 causes the ultrasonic probe 11 to perform the ultrasonic scanning while changing the position of the cross section having the smaller initial long axis length and determines the cross section at a position at which the first differential value is minimum. For example, when the initial long axis length of the A4C image is smaller, the scan control function 174 changes the position and the angle of the cross section of the A4C image and causes the ultrasonic probe 11 to perform the ultrasonic scanning on the changed cross section. For example, the scan control function 174 changes the position and the angle of the cross section of the A4C image in the direction perpendicular to the cross section of the A2C image. The scan control function 174 calculates the first differential value using the long axis length that is calculated from the cross section after being changed every time the cross section is changed. The scan control function 174 determines the A4C cross section at a position at which the first differential value is minimum.

At step S408, the scan control function 174 causes the ultrasonic probe 11 to perform the ultrasonic scanning while changing the position of the cross section having the larger initial long axis length and determines the cross section at a position at which the first differential value is minimum. For example, when the initial long axis length of the A2C image is larger, the scan control function 174 changes the position and the angle of the cross section of the A2C image and causes the ultrasonic probe 11 to perform the ultrasonic scanning on the changed cross section. For example, the scan control function 174 changes the position and the angle of the cross section of the A2C image in the direction perpendicular to the cross section of the A4C image. The scan control function 174 calculates the first differential value using the long axis length that is calculated from the cross section after being changed every time the cross section is changed. The scan control function 174 determines the A2C cross section at a position at which the first differential value is minimum.

At step S409, the scan control function 174 calculates a second differential value between the initial long axis length and the current long axis length for the cross section having the larger initial long axis length. For example, when the initial long axis length of the A2C image is smaller, the scan control function 174 calculates, as the second differential value, an absolute value of the difference between the initial long axis length of the A2C image that has been calculated by the processing at step S405 and the long axis length of the A2C image that has been calculated by the processing at step S409.

At step S410, the scan control function 174 determines whether the second differential value is lower than a threshold. When the determination at step S410 is negative, the scan control function 174 returns the process to the processing at step S407. The determination whether the second differential value is lower than the threshold is made because it is considered that a sufficiently long long axis can be provided, when variation of the larger long axis length is small.

When the determination at step S410 is positive, at step. S411, the scan control function 174 notifies the operator of finish of the processing. That is to say, the scan control function 174 determines the two cross sections determined by the pieces of processing at step S407 and step S408 as the cross sections of the A4C image and the A2C image. For example, the storage function 173 stores the pieces of ultrasonic image data of the determined A4C image and A2C image in the storage circuitry 160.

Thus, the ultrasonic diagnostic apparatus 1 in the fourth embodiment automatically changes the positions of the cross sections of the A4C image and the A2C image to decrease the difference between the long axis length of the A4C image and the long axis length of the A2C image and offers cross sections at the positions with the small difference therebetween to the operator. This notification enables the operator to automatically provide the cross section having the largest long axis length among the cross sections that are provided while the operator holds the ultrasonic probe 11 at a position in contact with the body surface of the subject P.

The contents as described in the first embodiment and the second embodiment can be also applied to the fourth embodiment except that the operator is notified of the cross section of the A4C image or the A2C image having the smaller long axis length. For example, the output control function 172 may display the image 30 as described in the first embodiment on the current ultrasonic image that is displayed substantially real time.

Other Embodiments

The embodiment may be carried out in various different modes other than the above-mentioned embodiments.

For example, the components of the devices as illustrated in the drawings are conceptual functionally and are not necessarily required to be configured as illustrated in the drawings physically. That is to say, specific forms of distribution and integration of the devices are not limited to those as illustrated in the drawings, and all of or a part of them can be configured to be distributed or integrated functionally or physically based on a desired unit depending on various loads and usage conditions. Furthermore, all of or any part of processing functions operating in the devices can be implemented by a central processing unit (CPU) and a computer program that is analyzed and executed by the CPU or can be implemented as hardware by a wired logic.

Furthermore, all of or a part of processing that have been described to be performed automatically among the pieces of processing as described in the first embodiment to the fourth embodiment and the modifications can be performed manually. Alternatively, all of or a part of processing that have been described to be performed manually among the pieces of processing as described in the first embodiment to the fourth embodiment and the modifications can be performed automatically by a known method. In addition, information including processing procedures, control procedures, specific names, and pieces of data of various types and parameters as described in the above-described document and drawings can be changed as appropriate unless otherwise specified.

A control method of the ultrasonic diagnostic apparatus as described in the first embodiment to the fourth embodiment and the modifications can be also executed by executing a previously prepared control program by a computer such as a personal computer and a workstation. The control program can be distributed through a network such as the Internet. The ultrasonic imaging method can be also executed by being recorded in a computer readable recording medium such as a hard disk, a flexible disk (ED), a compact disc read only memory (CD-ROM), a magneto-optic disc (MO), and a digital versatile disc (DVD) and being read from the recording medium by the computer.

According to at least one of the above-described embodiments, the desired cross sect on can be provided accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:

an ultrasonic probe as a two-dimensional array probe configured to perform ultrasonic scanning on an apical four-chamber view (A4C) cross section and perform ultrasonic scanning on an apical two-chamber view (A2C) cross section;

image generation circuitry configured to generate first ultrasonic image data corresponding to the A4C cross section and second ultrasonic image data corresponding to the A2C cross section; and processing circuitry configured to calculate a first characteristic amount of a structure that is detected from the first ultrasonic image data and a second characteristic amount of the structure that is detected from the second ultrasonic image data, and cause the ultrasonic probe to perform ultrasonic scanning in which a position of the A4C cross section or the A2C cross section is changed to decrease a difference between the first characteristic amount and the second characteristic amount, wherein the processing circuitry calculates, as the first characteristic amount of the structure, a first long axis length that is a length of a long axis of a heart that is detected from the first ultrasonic image data and, as the second characteristic amount of the structure, a second long axis length that is a length of the long axis of the heart that is detected from the second ultrasonic image data, and the processing circuitry causes the ultrasonic probe to perform ultrasonic scanning in which the position of the A4C cross section is changed when the first long axis length among the first long axis length and the second long axis length is smaller and causes the ultrasonic probe to perform ultrasonic scanning in which the position of the A2C cross section is changed when the second long axis length is smaller.

2. The ultrasonic diagnostic apparatus according to claim 1, wherein the processing circuitry outputs information based on a comparison result of the first characteristic amount and the second characteristic amount.

3. The ultrasonic diagnostic apparatus according to claim 2, wherein the processing circuitry specifies the first ultrasonic image data and the second ultrasonic image data in a predetermined cardiac phase based on electrocardiogram signals that are detected from a subject and calculates the characteristic amount from each of the specified first ultrasonic image data and second ultrasonic image data, and the processing circuitry outputs information based on a comparison result of the characteristic amounts in the cardiac phase.

4. The ultrasonic diagnostic apparatus according to claim 2, wherein the processing circuitry simultaneously displays images based on the first ultrasonic image data and the second ultrasonic image data generated by the image generation circuitry and images based on a first ultrasonic image data and a second ultrasonic image data previously generated.

5. The ultrasonic diagnostic apparatus according to claim 4, wherein the processing circuitry synthesizes cardiac cycles of the images displayed simultaneously based on electrocardiogram signals that are detected from the subject.

6. A control method comprising:

generating first ultrasonic image data corresponding to an apical four-chamber view (A4C) cross section on which an ultrasonic probe that is a two-dimensional array probe has performed ultrasonic scanning and second ultrasonic image data corresponding to an apical two-chamber view (A2C) cross section;

calculating a first characteristic amount of a structure that is detected from the first ultrasonic image data and a second characteristic amount of the structure that is detected from the second ultrasonic image data; and causing the ultrasonic probe to perform the ultrasonic scanning in which a position of the A4C cross section or the A2C cross section is changed to decrease a difference between the first characteristic amount and the second characteristic amount, wherein the calculating process calculates, as the first characteristic amount of the structure, a first long axis length that is a length of a long axis of a heart that is detected from the first ultrasonic image data and, as the second characteristic amount of the structure, a second long axis length that is a length of the long axis of the heart that is detected from the second ultrasonic image data, and the causing process causes the ultrasonic probe to perform ultrasonic scanning in which the position of the A4C cross section is changed when the first long axis length among the first long axis length and the second long axis length is smaller and causes the ultrasonic probe to perform ultrasonic scanning in which the position of the A2C cross section is changed when the second long axis length is smaller.

* * * * *